(12) United States Patent
Widner et al.

(10) Patent No.: US 6,255,076 B1
(45) Date of Patent: Jul. 3, 2001

(54) METHODS FOR PRODUCING A POLYPEPTIDE IN A BACILLUS CELL

(75) Inventors: William Widner; Alan Sloma; Michael D. Thomas, all of Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/258,377

(22) Filed: Feb. 26, 1999

Related U.S. Application Data

(63) Continuation-in-part of application No. 09/031,442, filed on Feb. 26, 1998, now Pat. No. 5,955,310.

(51) Int. Cl.[7] .............................. C12P 21/06; C12N 9/00; C12N 1/20; C12N 15/00; C12N 5/00
(52) U.S. Cl. ..................... 435/69.1; 435/320.1; 435/325; 435/252.31; 435/252.3; 435/183; 435/201; 435/209; 435/207; 435/198; 435/194; 435/195
(58) Field of Search ................................ 435/69.1, 320.1, 435/252.31, 252.3, 183, 194, 201, 207, 209, 198, 195

(56) References Cited

FOREIGN PATENT DOCUMENTS

WO 94/25612    11/1994   (WO) .

OTHER PUBLICATIONS

Agaisse et al., Molecular Biology, 13 (1), pp. 97–107, (1994).
Hue et al., Journal of Bacteriology, vol. 177, No. 12, pp. 3465–3471, (1995).
Ichikawa et al., FEMS Microbiology Letters, 111, pp. 219–224, (1993).

*Primary Examiner*—Rebecca E. Prouty
*Assistant Examiner*—Maryam Monshipouri
(74) *Attorney, Agent, or Firm*—Robert L. Starnes

(57) ABSTRACT

The present invention relates to methods for producing a polypeptide, comprising: (a) cultivating a Bacillus host cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and alternatively also (ii) an mRNA processing/stabilizing sequence located downstream of the tandem promoter and upstream of the nucleic acid sequence encoding the polypeptide; and (b) isolating the polypeptide from the cultivation medium. The present invention also relates to methods for producing a polypeptide, comprising: (a) cultivating a Bacillus host cell in a medium conducive for the production of the polypeptide, wherein the Bacillus cell comprises a nucleic acid construct comprising (i) a "consensus" promoter having the sequence TTGACA for the "−35" region and TATAAT for the "−10" region operably linked to a single copy of a nucleic acid sequence encoding the polypeptide and (ii) an mRNA processing/stabilizing sequence located downstream of the "consensus" promoter and upstream of the nucleic acid sequence encoding the polypeptide; and (b) isolating the polypeptide from the cultivation medium.

23 Claims, 29 Drawing Sheets

```
                    SfiI
              GGCCT TAAGGGCCTG CAATCGATTG TTTGAGAAAA

GAAGAAGACC ATAAAAATAC CTTGTCTGTC ATCAGACAGG GTATTTTTTA

-35
                                    t                   a
TGCTGTCCAG ACTGTCCGCT GTGTAAAAAA AAGGAATAAA GGGGGGTTGT

-10
c           t                                        SacI
TATTATTTTA CTGATATGTA AAATATAATT TGTATAAGAA AATGGAGCTC
```

Fig. 21

METHODS FOR PRODUCING A POLYPEPTIDE IN A BACILLUS CELL

CROSS REFERENCE TO RELATED APPLICATIONS

This application is a continuation-in-part of application Ser. No. 09/031,442 filed Feb. 26, 1998 now U.S. Pat. No. 5,955,310 issued Sep. 21, 1999, the contents of which are fully incorporated herein by reference.

BACKGROUND OF THE INVENTION

1. Field of the Invention

The present invention relates to methods for producing a polypeptide in a bacterial cell.

2. Description of the Related Art

Bacilli are well established as host cell systems for the production of native and recombinant proteins. However, Bacillus host cells with the desirable traits of increased protein expression may not necessarily have the most desirable characteristics for commercial use.

Conventionally, maximal expression of a gene contained in a Bacillus cell is achieved by amplifying in the chromosome an expression cassette containing a single promoter operably linked to a gene of interest and an amplifiable selectable marker gene, e.g., an antibiotic resistance marker. The amplification leads to the production of multiple copies of the expression cassette and the selectable marker gene in the chromosome.

However, there are disadvantages associated with this approach. For example, it may not be possible to achieve saturating levels of mRNA by amplifying genes driven by single promoters. Also, the production of multiple copies of the expression cassette and the selectable marker gene in the chromosome of a cell may not be stable. Furthermore, the removal of the selectable marker genes without also losing the expression cassettes may not be technically feasible.

Ichikawa et al. (1993, *FEMS Microbiological Letters* 111: 219–224) disclose the extracellular production of cholera toxin B in *Bacillus brevis* containing an expression-secretiion vector with multiple promoters which mediate the expression of the gene encoding the mature cholera toxin B.

Agaisse and Lereclus (1994, *Molecular Microbiology* 13: 97–107) disclose a structural and functional analysis of the promoter region involved in the full expression of the cryIIIA toxin gene of *Bacillus thuringiensis*. WO 94/25612 discloses an mRNA stabilizer region downstream of the promoter and upstream of the coding sequence of the cryIIIA gene which increases expression of the gene.

Hue et al. (1995, *Journal of Bacteriology* 177: 3465–3471) disclose a 5' mRNA stabilizer sequence which stabilized several heterologous RNA sequences when present at the 5' end and increased expression of downstream coding sequences several-fold in *Bacillus subtilis*.

It is an object of the present invention to provide improved methods for producing a polypeptide in a Bacillus strain.

SUMMARY OF THE INVENTION

The present invention relates to methods for producing a polypeptide, comprising: (a) cultivating a Bacillus host cell in a medium conducive for the production of the polypeptide, wherein the Bacillus cell comprises a nucleic acid construct comprising (i) a tandem promoter in which each promoter sequence of the tandem promoter is operably linked to a nucleic acid sequence encoding the polypeptide and alternatively also (ii) an mRNA processing/stabilizing sequence located downstream of the tandem promoter and upstream of the nucleic acid sequence encoding the polypeptide; and (b) isolating the polypeptide from the cultivation medium.

The present invention also relates to Bacillus cells comprising a nucleic acid construct which comprises (i) a tandem promoter in which each promoter sequence of the tandem promoter is operably linked to a single copy of a nucleic acid sequence encoding a polypeptide and alternatively also (ii) an mRNA processing/stabilizing sequence located downstream of the tandem promoter and upstream of the nucleic acid sequence encoding the polypeptide.

The present invention also relates to methods for producing a polypeptide, comprising: (a) cultivating a Bacillus host cell in a medium conducive for the production of the polypeptide, wherein the Bacillus cell comprises a nucleic acid construct comprising (i) a "consensus" promoter having the sequence TTGACA for the "−35" region and TATAAT for the "−10" region operably linked to a single copy of a nucleic acid sequence encoding the polypeptide and (ii) an mRNA processing/stabilizing sequence located downstream of the "consensus" promoter and upstream of the nucleic acid sequence encoding the polypeptide; and (b) isolating the polypeptide from the cultivation medium.

The present invention also relates to Bacillus cells comprising a nucleic acid construct which comprises (i) a "consensus" promoter having the sequence TTGACA for the "−35" region and TATAAT for the "−10" region operably linked to a single copy of a nucleic acid sequence encoding a polypeptide and (ii) an mRNA processing/stabilizing sequence located downstream of the "consensus" promoter and upstream of the nucleic acid sequence encoding the polypeptide.

The present invention also relates to methods for producing a polypeptide, comprising: (a) cultivating a Bacillus cell in a medium conducive for the production of the polypeptide, wherein the Bacillus cell comprises a nucleic acid sequence encoding the polypeptide operably linked to a "consensus" amyQ promoter; and (b) isolating the polypeptide from the cultivation medium.

The present invention also relates to Bacillus cells comprising a nucleic acid construct which comprises (i) a "consensus" amyQ promoter operably linked to a single copy of a nucleic acid sequence encoding a polypeptide and (ii) an MnRNA processing/stabilizing sequence located downstream of the "consensus" amyQ promoter and upstream of the nucleic acid sequence encoding the polypeptide.

The present invention also relates to methods for producing selectable marker-free mutants of a Bacillus cell.

BRIEF DESCRIPTION OF THE FIGURES

FIG. 21 shows a nucleic acid sequence containing the "consensus" amyQ promoter.

DETAILED DESCRIPTION OF THE INVENTION

Figure 1:
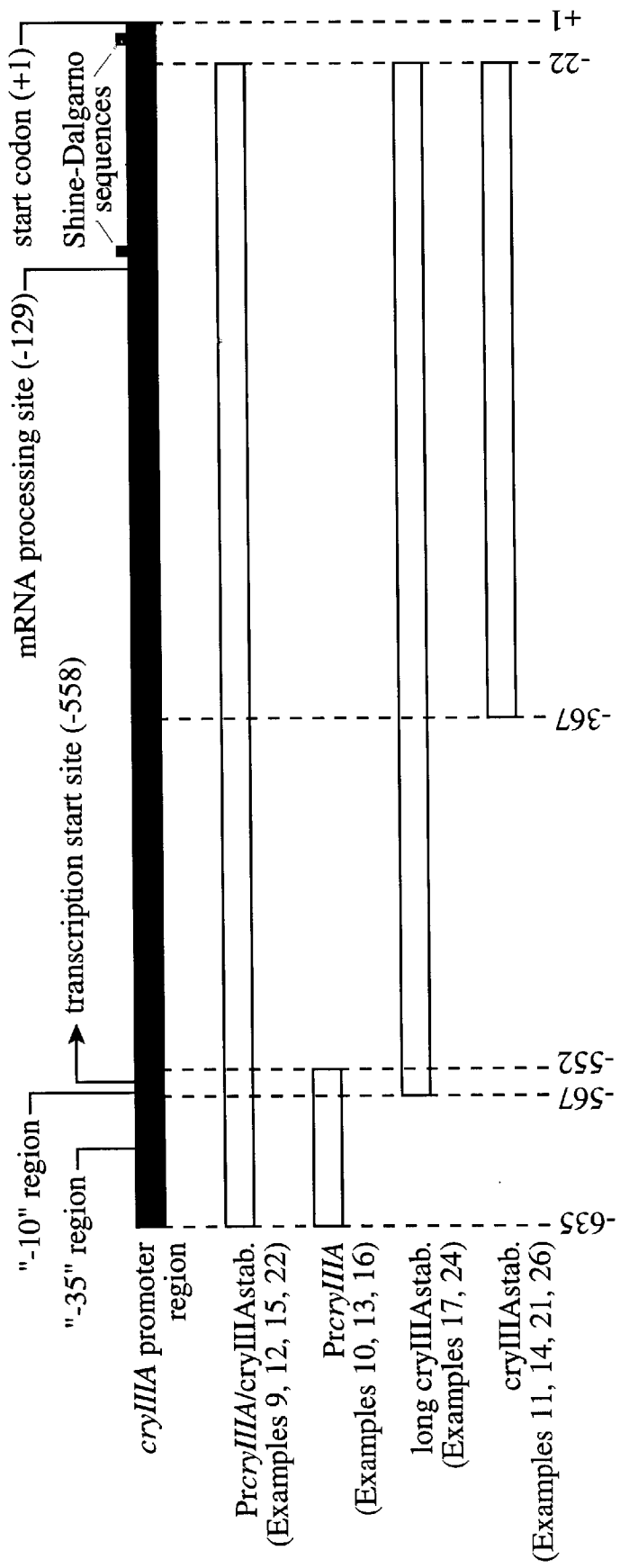
FIG. 1 shows a map of the cryIIfA promoter and the cryIIIA processing/stabilizing sequence.

In a first embodiment, the present invention relates to methods for producing a polypeptide, comprising: (a) cultivating a Bacillus cell in a medium conducive for the production of the polypeptide, wherein the Bacillus cell comprises a nucleic acid construct comprising (i) a tandem promoter in which each promoter sequence of the tandem promoter is operably linked to a single copy of a nucleic acid sequence encoding the polypeptide and alternatively also (ii) an mRNA processing/stabilizing sequence located downstream of the tandem promoter and upstream of the nucleic acid sequence encoding the polypeptide; and (b) isolating the polypeptide from the cultivation medium.

In a second embodiment, the present invention relates to methods for producing a polypeptide, comprising: (a) cultivating a Bacillus host cell in a medium conducive for the production of the polypeptide, wherein the Bacillus cell comprises a nucleic acid construct comprising (i) a "consensus" promoter operably linked to a single copy of a nucleic acid sequence encoding the polypeptide and (ii) an mRNA processing/stabilizing sequence located downstream of the "consensus" promoter and upstream of the nucleic acid sequence encoding the polypeptide; and (b) isolating the polypeptide from the cultivation medium.

In a third embodiment, the present invention relates to methods for producing a polypeptide, comprising: (a) cultivating a Bacillus cell in a medium conducive for the production of the polypeptide, wherein the Bacillus cell comprises a nucleic acid sequence encoding the polypeptide operably linked to a "consensus" amyQ promoter; and (b) isolating the polypeptide from the cultivation medium.

"Promoter" is defined herein as a nucleic acid sequence involved in the binding of RNA polymerase to initiate transcription of a gene. "Tandem promoter" is defined herein as two or more promoter sequences each of which is operably linked to a coding sequence and mediates the transcription of the coding sequence into mRNA. "Operably linked" is defined herein as a configuration in which a control sequence, e.g., a promoter sequence, is appropriately placed at a position relative to a coding sequence such that the control sequence directs the production of a polypeptide encoded by the coding sequence. "Coding sequence" is defined herein as a nucleic acid sequence which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence.

Each promoter sequence of the tandem promoter may be any nucleic acid sequence which shows transcriptional activity in the Bacillus cell of choice including a mutant, truncated, and hybrid promoter, and may be obtained from genes encoding extracellular or intracellular polypeptides either homologous or heterologous to the Bacillus cell. Each promoter sequence may be native or foreign to the nucleic acid sequence encoding the polypeptide and native or foreign to the Bacillus cell. The promoter sequences may be the same promoter sequence or different promoter sequences.

In a preferred embodiment, the promoter sequences may be obtained from a bacterial source. In a more preferred embodiment, the promoter sequences may be obtained from a gram positive bacterium such as a Bacillus strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a Streptomyces strain, e.g., *Streptomyces lividans* or *Streptomyces murinus*; or from a gram negative bacterium, e.g., *E. coli* or Pseudomonas sp.

An example of a suitable promoter for directing the transcription of a nucleic acid sequence in the methods of the present invention is the promoter obtained from the *E. coli* lac operon. Another example is the promoter of the *Streptomyces coelicolor* agarase gene (dagA). Another example is the promoter of the *Bacillus lentus* alkaline protease gene (aprH). Another example is the promoter of the *Bacillus lichenifonnis* alkaline protease gene (subtilisin Carlsberg gene). Another example is the promoter of the *Bacillus subtilis* levansucrase gene (sacB). Another example is the promoter of the *Bacillus subtilis* alpha-amylase gene (amyE). Another example is the promoter of the *Bacillus licheniformis* alpha-amylase gene (amyL). Another example is the promoter of the *Bacillus stearothennophilus* maltogenic amylase gene (amyM). Another example is the promoter of the *Bacillus amyloliquefaciens* alpha-amylase gene (amyQ). Another example is a "consensus" promoter having the sequence TTGACA for the "–35" region and TATAAT for the "–10" region. Another example is the promoter of the *Bacillus licheniformis* penicillinase gene (penP). Another example are the promoters of the *Bacillus subtilis* xylA and xylB genes. Another example is the promoter of the *Bacillus thuringiensis* subsp. *tenebrionis* CryIIIA gene (cryIIIA, SEQ ID NO. 21) or portions thereof. Another example is the promoter of the prokaryotic beta-lactamase gene (Villa-Kamaroff et al., 1978, *Proceedings of the National Academy of Sciences USA* 75:3727–3731). Another example is the promoter of the spol bacterial phage promoter. Another example is the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook, Fritsch, and Maniatus, 1989, *Molecular Cloning, A Laboratory Manual*, 2d edition, Cold Spring Harbor, N.Y.

The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the Bacillus cell.

In a preferred embodiment, the tandem promoter contains at least the amyQ promoter of the *Bacillus amyloliquefaciens* alpha-amylase gene. In another preferred embodiment, the tandem promoter contains at least a "consensus" promoter having the sequence TTGACA for the "–35" region and TATAAT for the "–10" region. In another preferred embodiment, the tandem promoter contains at least the amyL promoter of the *Bacillus licheniformis* alpha-amylase gene. In another preferred embodiment, the tandem promoter contains at least the cryIIIA promoter or portions thereof (Agaisse and Lereclus, 1994, supra).

In a more preferred embodiment, the tandem promoter contains at least the amyL promoter and the cryIIIA promoter. In another more preferred embodiment, the tandem promoter contains at least the amyQ promoter and the cryIIIA promoter. In another more preferred embodiment, the tandem promoter contains at least a "consensus" promoter having the sequence TTGACA for the "–35" region and TATAAT for the "–10" region and the cryIIIA promoter. In another more preferred embodiment, the tandem promoter contains at least two copies of the amyL promoter. In another more preferred embodiment, the tandem promoter contains at least two copies of the amyQ promoter. In another more preferred embodiment, the tandem promoter contains at least two copies of a "consensus" promoter having the sequence TTGACA for the "–35" region and TATAAT for the "–10" region. In another more preferred embodiment, the tandem promoter contains at least two copies of the cryIIIA promoter.

The construction of a "consensus" promoter may be accomplished by site-directed mutagenesis to create a promoter which conforms more perfectly to the established consensus sequences for the "–10" and "–35" regions of the vegetative "sigma A-type" promoters for *Bacillus subtilis* (Voskuil et al., 1995, *Molecular Microbiology* 17: 271–279). The consensus sequence for the "–35" region is TTGACA and for the "–10" region is TATAAT. The consensus promoter may be obtained from any promoter which can function in a Bacillus host cell.

In a preferred embodiment, the "consensus" promoter is obtained from a promoter obtained from the *E. coli* lac operon, *Streptomyces coelicolor* agarase gene (dagA), *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothernophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA, SEQ ID NO. 21) or portions thereof, or prokaryotic beta-lactamase gene spol bacterial phage promoter.

In a more preferred embodiment, the "consensus" promoter is obtained from *Bacillus amyloliquefaciens* alpha-amylase gene (amyQ). In a most preferred embodiment, the consensus promoter is the "consensus" amyQ promoter contained in nucleotides 1 to 185 of SEQ ID NO. 26 or SEQ ID NO. 27. In another most preferred embodiment, the consensus promoter is the short "consensus" amyQ promoter contained in nucleotides 86 to 185 of SEQ ID NO. 26 or SEQ ID NO. 27. The "consensus" amyQ promoter of SEQ ID NO. 26 contains the following mutations of the nucleic acid sequence containing the wild-type amyQ promoter (SEQ ID NO. 25): T to A and T to C in the –35 region (with respect to the transcription start site) at positions 135 and 136, respectively, and an A to T change in the –10 region at position 156 of SEQ ID NO. 25. The "consensus" amyQ promoter (SEQ ID NO. 27) further contains a T to A change at position 116 approximately 20 base pairs upstream of the –35 region as shown in FIG. 21 (SEQ ID NO. 27). This change apparently had no detrimental effect on promoter function since it is well removed from the critical –10 and –35 regions.

"An mRNA processing/stabilizing sequence" is defined herein as a sequence located downstream of one or more promoter sequences and upstream of a coding sequence to which each of the one or more promoter sequences are operably linked such that all mRNAs synthesized from each promoter sequence may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, supra). The mRNA processing/stabilizing sequence is complementary to the 3' extremity of a bacterial 16S ribosomal RNA. In a preferred embodiment, the MrRNA processing/stabilizing sequence generates essentially single-size transcripts with a stabilizing sequence at the 5' end of the transcripts.

In a more preferred embodiment, the mRNA processing/stabilizing sequence is the *Bacillus thuringiensis* cryIIIA mRNA processing/stabilizing sequence disclosed in WO 94/25612 and Agaisse and Lereclus, 1994, supra, or portions thereof which retain the MRNA processing/stabilizing function. In another more preferred embodiment, the mRNA processing/stabilizing sequence is the *Bacillus subtilis* SP82 mRNA processing/stabilizing sequence disclosed in Hue et al., 1995, supra, or portions thereof which retain the mRNA processing/stabilizing function.

Figure 2:
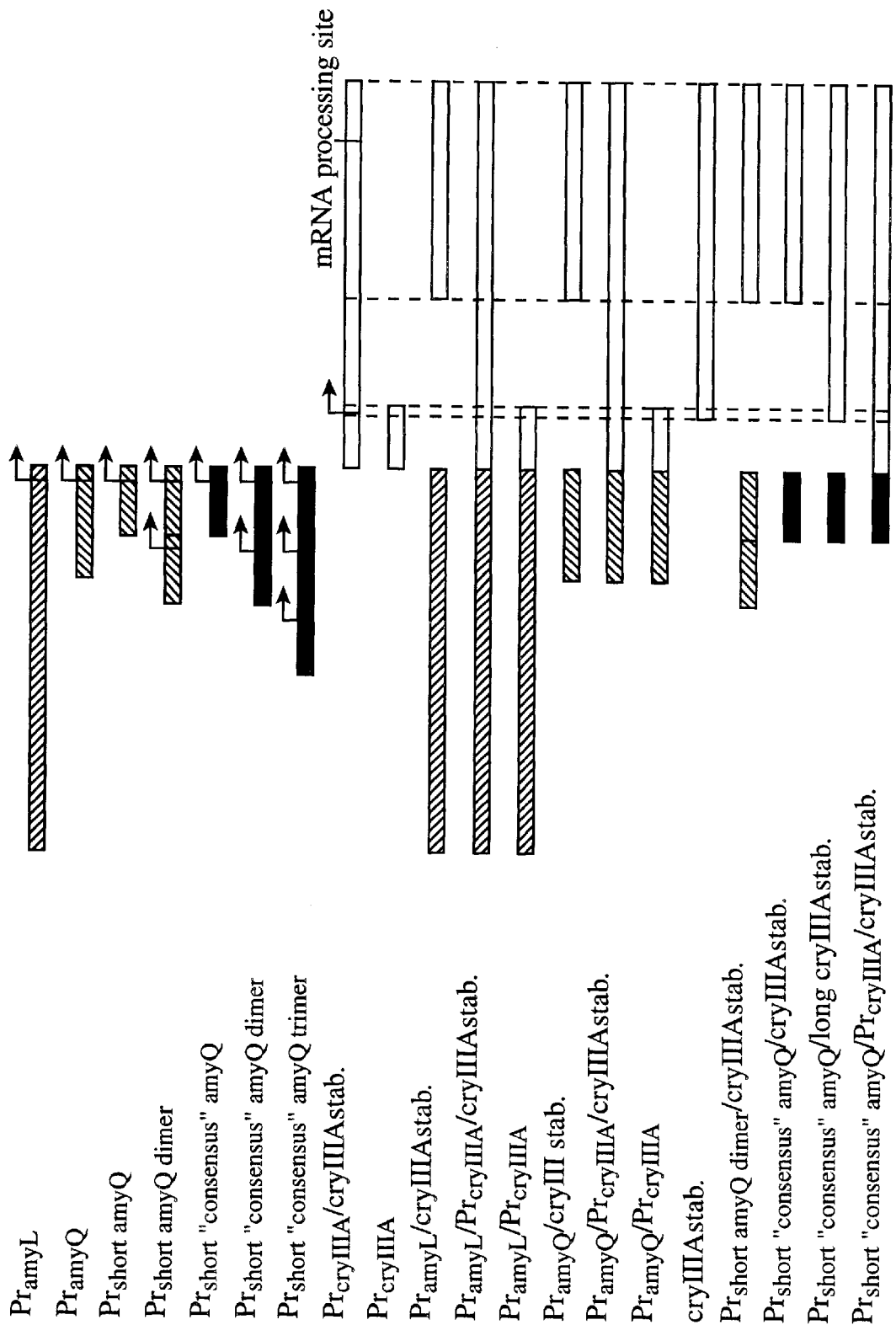
FIG. 2 shows schematically various constructions containing a tandem promoter and the cryIIIA mRNA processing/stabilizing sequence.

When the cryIIIA promoter and its mRNA processing/stabilizing sequence are employed in the methods of the present invention, a DNA fragment containing the sequence disclosed in WO 94/25612 and Agaisse and Lereclus, 1994, supra, delineated by nucleotides −635 to −22 (FIG. 1) (SEQ ID NO. 21), or portions thereof which retain the promoter and mRNA processing/stabilizing functions, may be used. The cryIIIA promoter is delineated by nucleotides −635 to −552 while the cryIIIA mRNA processing/stabilizing sequence is contained within nucleotides −551 to −22. In a preferred embodiment, the cryIIIA mRNA processing/stabilizing sequence is contained in a fragment comprising nucleotides −568 to −22. In another preferred embodiment, the cryIIIA mRNA processing/stabilizing sequence is contained in a fragment comprising nucleotides −367 to −21. Furthermore, DNA fragments containing only the cryIIIA promoter or only the cryIIIA mRNA processing/stabilizing sequence may be prepared using methods well known in the art to construct various tandem promoter and mRNA processing/stabilizing sequence combinations. In this embodiment, the cryIIIA promoter and its mRNA processing/stabilizing sequence are preferably placed downstream of the other promoter sequence(s) constituting the tandem promoter and upstream of the coding sequence of the gene of interest. Various constructions containing a tandem promoter and the cryIIIA mRNA processing/stabilizing sequence are shown in FIG. 2.

The Bacillus cell may contain one or more copies of the nucleic acid construct. In a preferred embodiment, the Bacillus cell contains a single copy of the nucleic acid construct.

The nucleic acid construct may further contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

A particular advantage of the present invention is that a Bacillus cell can be produced free of a selectable marker gene, i.e., after the introduction of the nucleic acid construct into the Bacillus cell, the selectable marker gene can be deleted from the Bacillus cell making the cell marker-free. The nucleic acid construct containing a single copy of the nucleic acid sequence encoding the polypeptide allows for the removal of the selectable marker gene to produce a Bacillus cell free of such a marker which may be preferable for regulatory and environmental reasons.

Gene deletion or replacement techniques may be used for the complete removal of the selectable marker gene. In such methods, the deletion of the selectable marker gene may be accomplished by homologous recombination using a plasmid which has been constructed to contiguously contain the 5' and 3' regions flanking the selectable marker gene. The contiguous 5' and 3' regions may be introduced into a Bacillus cell on a temperature-sensitive plasmid, e.g., pE194, in association with a second selectable marker at a permissive temperature to allow the plasmid to become established in the cell. The cell is then shifted to a non-permissive temperature to select for cells which have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, for example, Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C., 1993).

The polypeptide may be native or heterologous to the Bacillus cell. The term "polypeptide" is not meant herein to refer to a specific length of the encoded product and, therefore, encompasses peptides, oligopeptides, and proteins. The polypeptide may also be a naturally occurring allelic or engineered variant of a polypeptide.

Preferably, the polypeptide is a hormone or variant thereof, enzyme, receptor or portion thereof, antibody or portion thereof, or reporter. In a more preferred embodiment, the polypeptide is an oxidoreductase. In another more preferred embodiment, the polypeptide is a transferase. In another more preferred embodiment, the polypeptide is a hydrolase. In another more preferred embodiment, the polypeptide is a lyase. In another more preferred embodiment, the polypeptide is an isomerase. In another more preferred embodiment, the polypeptide is a ligase.

In an even more preferred embodiment, the polypeptide is an aminopeptidase. In another even more preferred embodiment, the polypeptide is an amylase. In another even more preferred embodiment, the polypeptide is a carbohydrase. In another even more preferred embodiment, the polypeptide is a carboxypeptidase. In another even more preferred embodiment, the polypeptide is a catalase. In another even more preferred embodiment, the polypeptide is a cellulase. In another even more preferred embodiment, the polypeptide is a chitinase. In another even more preferred embodiment, the polypeptide is a cutinase. In another even more preferred embodiment, the polypeptide is a cyclodextrin glycosyltransferase. In another even more preferred embodiment, the polypeptide is a deoxyribonuclease. In another even more preferred embodiment, the polypeptide is an esterase. In another even more preferred embodiment, the polypeptide is an alpha-galactosidase. In another even more preferred embodiment, the polypeptide is a beta-galactosidase. In another even more preferred embodiment, the polypeptide is a glucoamylase. In another even more preferred embodiment, the polypeptide is an alpha-glucosidase. In another even more preferred embodiment, the polypeptide is a beta-glucosidase. In another even more preferred embodiment, the polypeptide is an invertase. In another even more preferred embodiment, the polypeptide is a laccase. In another even more preferred embodiment, the polypeptide is a lipase. In another even more preferred embodiment, the polypeptide is a mannosidase. In another even more preferred embodiment, the polypeptide is a mutanase. In another even more preferred embodiment, the polypeptide is an oxidase. In another even more preferred embodiment, the polypeptide is a pectinolytic enzyme. In another even more preferred embodiment, the polypeptide is a peroxidase. In another even more preferred embodiment, the polypeptide is a phytase. In another even more preferred embodiment, the polypeptide is a polyphenoloxidase. In another even more preferred embodiment, the polypeptide is a proteolytic enzyme. In another even more preferred embodiment, the polypeptide is a ribonuclease. In another even more preferred embodiment, the polypeptide is a transglutaminase. In another even more preferred embodiment, the polypeptide is a xylanase.

In a most preferred embodiment, the polypeptide is a serine protease, for example, a subtilisin. In another most preferred embodiment, the polypeptide is a maltogenic amylase. In another most preferred embodiment, the polypeptide is a pullulanase.

The methods of the present invention may also be used for the recombinant production of polypeptides which are native to the Bacillus cell. The present invention also encompasses, within the scope of the term "heterologous polypeptide", such recombinant production of native polypeptides, to the extent that such expression involves the use of genetic elements not native to the Bacillus cell, or use of native elements which have been manipulated to function in a manner not normally occurring in the host cell.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the Bacillus cell.

The construction of a Bacillus cell comprising a tandem or "consensus" promoter and alternatively also an mRNA processing/stabilizing sequence, operably linked to a nucleic acid sequence encoding a polypeptide of interest may be accomplished by modifying an isolated nucleic acid sequence encoding the polypeptide using methods well known in the art to operably link the promoter and alternatively also the mRNA processing/stabilizing sequence to the nucleic acid sequence, inserting the modified sequence into a vector, and introducing the vector into the Bacillus cell's chromosome by homologous recombination or into the Bacillus cell as an extrachromosomal autonomously replicating element, e.g., plasmid. However, it will be understood that the nucleic acid sequence may also be manipulated in vivo in the Bacillus cell using methods well known in the art.

In the methods of the present invention, a nucleic acid sequence encoding a polypeptide of interest may be native or foreign to the Bacillus cell. A foreign nucleic acid sequence encoding a heterologous polypeptide may be obtained from any prokaryotic, eukaryotic, or other source, e.g., archaebacteria. In a preferred embodiment, the nucleic acid sequence is obtained from a bacterial strain, such as a gram-negative or a gram-positive bacterial cell. In a more preferred embodiment, the nucleic acid sequence encoding the polypeptide is obtained from a Bacillus cell. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide are well known in the art and include, for example, isolation from genomic DNA, preparation from cDNA, or a combination thereof. The cloning of the nucleic acid sequences from such genomic DNA can be effected, e.g., by using antibody screening of expression libraries to detect cloned DNA fragments with shared structural features or the well known polymerase chain reaction (PCR). See, for example, Innis et al., 1990, *PCR Protocols: A Guide to Methods and Application*, Academic Press, New York. Other nucleic acid amplification procedures such as ligase chain reaction (LCR), ligated activated transcription (LAT), and nucleic acid sequence-based amplification (NASBA) may be used. The cloning procedures may involve excision and isolation of a desired nucleic acid fragment comprising the nucleic acid sequence encoding the polypeptide, insertion of the fragment into a vector molecule, and incorporation of the recombinant vector into a Bacillus cell where clones of the nucleic acid sequence will be replicated. The nucleic acid sequence may be of genomic, cDNA, RNA, semisynthetic, synthetic origin, or any combinations thereof.

An isolated nucleic acid sequence encoding a polypeptide of interest may then be manipulated to produce a nucleic acid construct by operably linking the nucleic acid sequence to a tandem or "consensus" promoter and alternatively also to an mRNA processing/stabilizing sequence, as well as one or more additional control sequences which direct the expression of the coding sequence in a Bacillus cell under conditions compatible with the control sequences. Expression will be understood to include any step involved in the production of the polypeptide including, but not limited to, transcription, post-transcriptional modification, translation, post-translational modification, and secretion. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. In addition to the tandem or "consensus" promoter, described earlier, such control sequences include, but are not limited to, a leader, a signal sequence, and a transcription terminator. The control sequences may be provided with linkers for the purpose of introducing specific restriction sites facilitating ligation of the control sequences with the coding region of the nucleic acid sequence encoding a polypeptide.

The control sequence may also be a suitable transcription terminator sequence, a sequence recognized by a Bacillus cell to terminate transcription. The terminator sequence is operably linked to the 3' terminus of the nucleic acid sequence encoding the polypeptide. Any terminator which is functional in the Bacillus cell of choice may be used in the present invention.

The control sequence may also be a suitable leader sequence, a nontranslated region of an mRNA which is important for translation by the Bacillus cell. The leader sequence is operably linked to the 5' terminus of the nucleic acid sequence encoding the polypeptide. Any leader sequence which is functional in the Bacillus cell of choice may be used in the present invention.

The control sequence may also be a signal peptide coding region that codes for an amino acid sequence linked to the amino terminus of the polypeptide which directs the expressed polypeptide into the cell's secretory pathway. The signal peptide coding region may be native to the polypeptide or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a Bacillus species. However, any signal peptide coding region capable of directing the expressed polypeptide into the secretory pathway of a Bacillus cell of choice may be used in the present invention.

An effective signal peptide coding region for Bacillus cells is the signal peptide coding region obtained from the Bacillus NCIB 11837 maltogenic amylase gene, *Bacillus stearothermophilus* alpha-amylase gene, *Bacillus licheniformis* subtilisin gene, *Bacillus licheniformis* beta-lactamase gene, *Bacillus stearothermophilus* neutral protease genes (nprT, nprS, nprM), and *Bacillus subtilis* prsA gene. Further signal peptides are described by Simonen and Palva, 1993, *Microbiological Reviews* 57: 109–137.

In the methods of the present invention, a recombinant expression vector comprising a nucleic acid sequence encoding a polypeptide of interest, a tandem or "consensus" promoter and alternatively also an mRNA processing/stabilizing sequence, and transcriptional and translational stop signals may be used for the recombinant production of a polypeptide. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with a tandem or "consensus" promoter and alternatively also an mRNA processing/stabilizing sequence, and any other appropriate control sequences for expression, and possibly secretion.

The recombinant expression vector may be any vector which can be conveniently subjected to recombinant DNA procedures and can bring about the expression of the nucleic acid sequence on introduction into a Bacillus cell. The choice of the vector will typically depend on the compatibility of the vector with the Bacillus cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the Bacillus cell, is integrated into the genome and replicated together with the chromosome(s) into which it has been integrated. The vector system may be a single vector or plasmid or two or more vectors or plasmids, or a transposon.

"Introduction" means introducing a vector comprising the nucleic acid sequence into a Bacillus cell so that the vector is maintained as a chromosomal integrant or as a self-replicating extrachromosomal vector. Integration is generally considered to be an advantage as the nucleic acid sequence is more likely to be stably maintained in the cell. Integration of the vector into the chromosome occurs by homologous recombination, non-homologous recombination, or transposition.

The introduction of an expression vector into a Bacillus cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5271–5278).

For integration, the vector may rely on the nucleic acid sequence encoding the polypeptide or any other element of the vector for stable integration of the vector into the genome by homologous recombination. The vector may contain additional nucleic acid sequences for directing integration by homologous recombination into the genome of the Bacillus cell. The additional nucleic acid sequences enable the vector to be integrated into the Bacillus cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the Bacillus cell. Furthermore, the integrational elements may be non-encoding or encoding nucleic acid sequences.

For autonomous replication, the vector may further comprise an origin of replication enabling the vector to replicate autonomously in the Bacillus cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. The origin of replication may be one having a mutation to make its function temperature-sensitive in the Bacillus cell (see, e.g., Ehrlich, 1978, *Proceedings of the National Academy of Sciences USA* 75:1433).

The procedures used to ligate the elements described above to construct the recombinant expression vectors are well known to one skilled in the art (see, e.g., Sambrook et al., 1989, supra).

In the methods of the present invention, the Bacillus cell may be a wild-type Bacillus cell or a mutant thereof. Furthermore, the Bacillus cell may be an alkalophilic or a thermophilic Bacillus. In a preferred embodiment, the Bacillus cell is a *Bacillus alkalophilus* cell. In another preferred embodiment, the Bacillus cell is a *Bacillus amyloliquefaciens* cell. In another preferred embodiment, the Bacillus cell is a *Bacillus brevis* cell. In another preferred embodiment, the Bacillus cell is a *Bacillus circulans* cell. In another preferred embodiment, the Bacillus cell is a *Bacillus clausii* cell. In another preferred embodiment, the Bacillus cell is a *Bacillus caogulans* cell. In another preferred embodiment, the Bacillus cell is a *Bacillus firmus* cell. In another preferred embodiment, the Bacillus cell is a *Bacillus lautus* cell. In another preferred embodiment, the Bacillus cell is a *Bacillus lentus* cell. In another preferred embodiment, the Bacillus cell is a *Bacillus licheniformis* cell. In another preferred embodiment, the Bacillus cell is a *Bacillus megaterium* cell. In another preferred embodiment, the Bacillus cell is a *Bacillus pumilus* cell. In another preferred embodiment, the Bacillus cell is a *Bacillus stearothennophilus* cell. In another preferred embodiment, the Bacillus cell is a *Bacillus subtilis* cell. In another preferred embodiment, the Bacillus cell is a *Bacillus thuringiensis* cell.

In the methods of the present invention, the Bacillus cell may be a recombinant cell comprising, for example, a nucleic acid sequence encoding a heterologous polypeptide.

The cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The polypeptides may be detected using methods known in the art that are specific for the polypeptides. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

In the methods of the present invention, the Bacillus cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a Bacillus cell containing only one of the promoter sequences of the tandem or "consensus" promoter operably linked to a nucleic acid sequence encoding the polypeptide when cultured under identical production conditions.

The resulting polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, New York, 1989).

The present invention also relates to Bacillus cells comprising a tandem promoter in which each promoter sequence of the tandem promoter is operably linked to a single copy of a nucleic acid sequence encoding a polypeptide and alternatively also an mRNA processing/stabilizing sequence located downstream of the tandem promoter and upstream of the nucleic acid sequence encoding the polypeptide. In a preferred embodiment, the Bacillus cell is free of a selectable marker gene.

The present invention also relates to Bacillus cells comprising a nucleic acid construct which comprises (i) a "consensus" promoter operably linked to a single copy of a nucleic acid sequence encoding a polypeptide and (ii) an mRNA processing/stabilizing sequence located downstream of the "consensus" promoter and upstream of the nucleic acid sequence encoding the polypeptide.

The present invention also relates to Bacillus host cells comprising a nucleic acid construct comprising one or more copies of a "consensus" amyQ promoter operably linked to a single copy of a nucleic acid sequence encoding the polypeptide.

The present invention also relates to methods for obtaining a Bacillus host cell, comprising introducing into a Bacillus cell a nucleic acid construct comprising (i) a tandem promoter in which each promoter sequence of the tandem promoter is operably linked to a single copy of a nucleic acid sequence encoding a polypeptide and alternatively also (ii) an mRNA processing/stabilizing sequence located downstream of the tandem promoter and upstream of the nucleic acid sequence encoding the polypeptide.

The present invention also relates to methods for obtaining a Bacillus host cell, comprising introducing into a Bacillus cell a nucleic acid construct comprising (i) a "consensus" promoter operably linked to a single copy of a nucleic acid sequence encoding the polypeptide and (ii) an mRNA processing/stabilizing sequence located downstream of the "consensus" promoter and upstream of the nucleic acid sequence encoding the polypeptide.

The present invention also relates to methods for obtaining a Bacillus host cell, comprising introducing into a Bacillus cell a nucleic acid construct comprising one or more copies of a "consensus" amyQ promoter operably linked to a single copy of a nucleic acid sequence encoding the polypeptide.

The present invention also relates to methods for producing a selectable marker-free mutant of a Bacillus cell, comprising deleting a selectable marker gene of the Bacillus cell, wherein the Bacillus cell comprises a nucleic acid construct comprising (i) a tandem promoter in which each promoter sequence of the tandem promoter is operably linked to a single copy of a nucleic acid sequence encoding a polypeptide and alternatively also (ii) an mRNA processing/stabilizing sequence located downstream of the tandem promoter and upstream of the nucleic acid sequence encoding the polypeptide.

The present invention also relates to methods for producing a selectable marker-free mutant of a Bacillus cell, comprising deleting a selectable marker gene of the Bacillus cell, wherein the Bacillus cell comprises a nucleic acid construct comprising (i) a "consensus" promoter operably linked to a single copy of a nucleic acid sequence encoding the polypeptide and (ii) an mRNA processing/stabilizing sequence located downstream of the "consensus" promoter and upstream of the nucleic acid sequence encoding the polypeptide.

The present invention also relates to methods for producing a selectable marker-free mutant of a Bacillus cell, comprising deleting a selectable marker gene of the Bacillus cell, wherein the Bacillus cell comprises a nucleic acid construct comprising one or more copies of a "consensus" amyQ promoter operably linked to a single copy of a nucleic acid sequence encoding the polypeptide.

The present invention also relates to such selectable marker-free Bacillus mutants produced by the methods of the present invention.

The present invention also relates to an isolated nucleic acid sequence comprising the "consensus" amyQ promoter contained in SEQ ID NO. 26 or SEQ ID NO. 27.

The present invention is further described by the following examples which should not be construed as limiting the scope of the invention.

EXAMPLES

Bacterial Strains

E. coli DH5α, E. coli JM101, and Bacillus subtilis PL1801 spoIIE::Tn917 (amyE, apr, npr).

Primers and Oligos

All primers and oligos were synthesized on an Applied Biosystems Model 394 Synthesizer (Applied Biosystems, Inc., Foster City, Calif.) according to the manufacturer's instructions.

Example 1

Construction of Plasmid pDG268MCS pDG268 (Antoniewski, et al., 1990, *Journal of Bacteriology* 172: 86–93) was digested with Tth111I and EcoRI, and the digest was subjected to electrophoresis using a 0.7% agarose gel with 45 mM Tris-borate-1 mM EDTA (TBE). The largest plasmid fragment of approximately 6020 bp was excised from the gel and the DNA was recovered using the Qiaquick DNA purification kit (QIAGEN, Inc., Chatsworth, Calif.) according to the manufacturer's instructions. The recovered DNA was then ligated with the following synthetic polylinker shown below to introduce unique SfiI and BamHI sites into the plasmid.

Example 2

Figure 4:
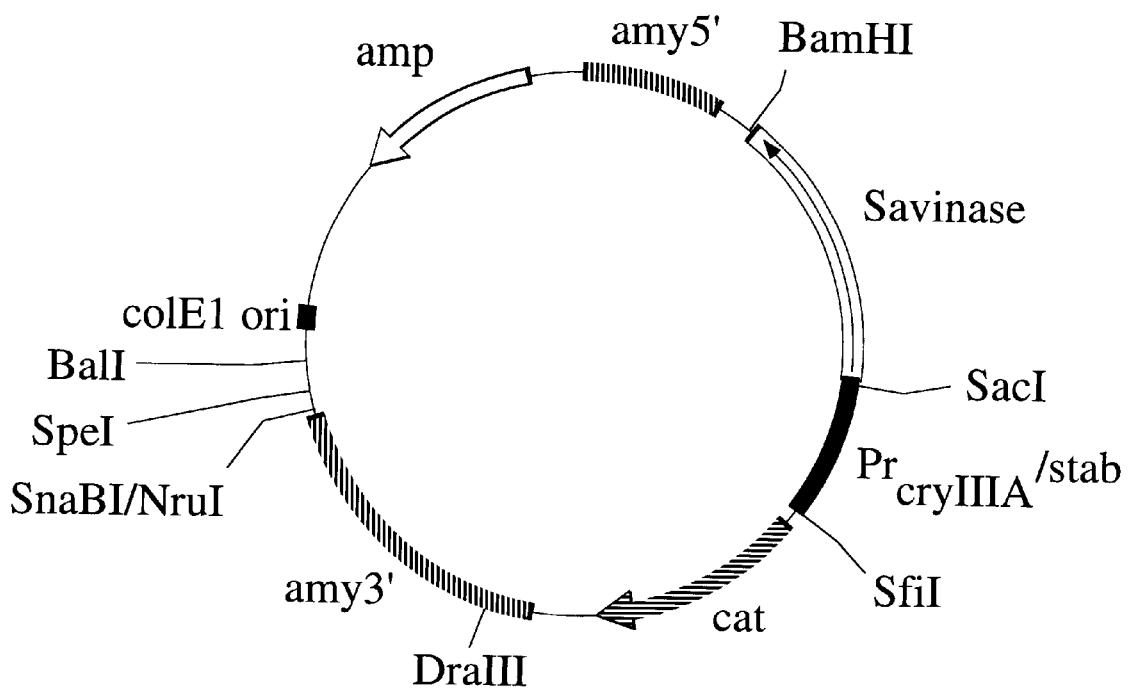
FIG. 4 shows a restriction map of pDG268MCSΔ-Pr$_{cryIIIA}$/cryIIIAstab/SAV.
Figure 12:
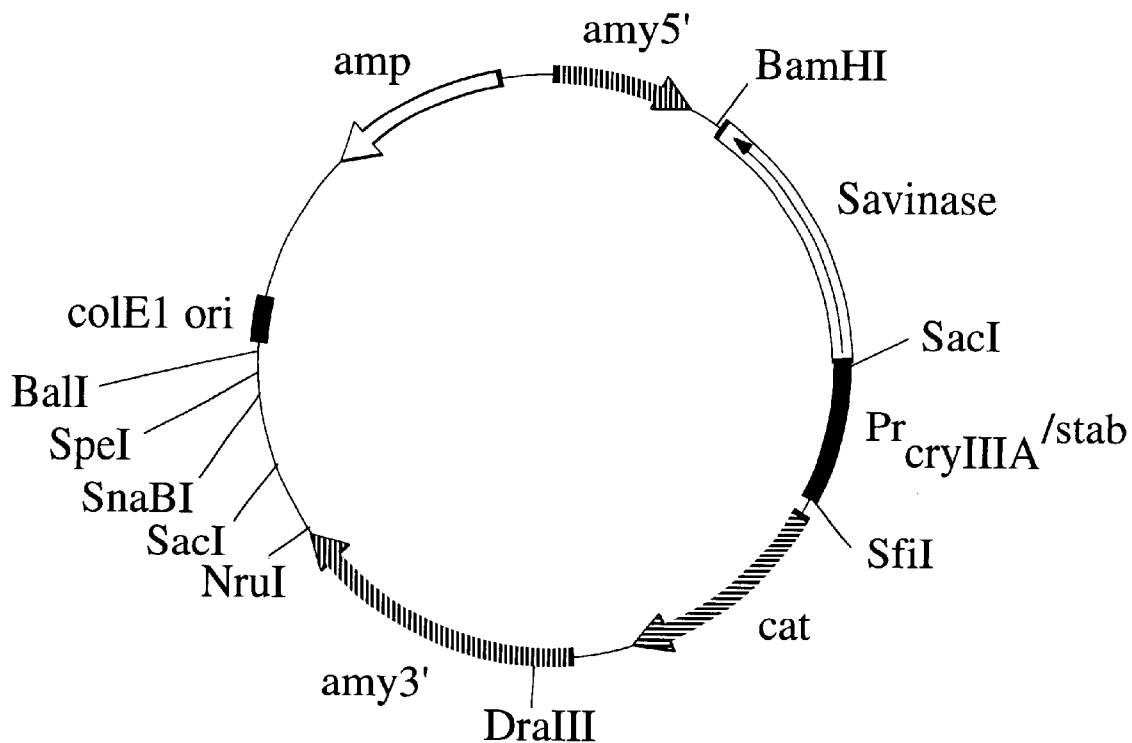
FIG. 12 shows a restriction map of pDG268MCS-Pr$_{cryIIIA}$/cryIIIAstab/SAV.

Construction of pDG268MCSΔ-Pr$_{cryIIIA}$/cryIIIAstab/SAV pDG268MCAΔ-Pr$_{cryIIA}$/cryIIIAstab/SAV was constructed to delete the SacI site in pDG268MCS of Example 1 to facilitate the swapping of promoter fragments engineered to contain a SacI site at their 3' end. pDG268MCS-Pr$_{cryIIIA}$/cryIIIAstab/SAV (see Example 9 and FIG. 12) was digested with SnaBI and NruI (both restriction sites flank the SacI site of the vector), ligated, and transformed into *E. coli* DH5α. Ampicillin resistant transformants were selected on LB plates supplemented with 100 μg of ampicillin per ml. Plasmid DNA was purified from several transformants and recovered as described in Example 1. The plasmid DNA was digested with SacI to identify plasmids which were deleted for the SacI site located in the vector sequence and thus cleaved only once due to the SacI site downstream of the cryIIIA promoter. Such a plasmid was identified and designated pDG268MCAΔ-Pr$_{cryIIIA}$/cryIIIAstab/SAV (FIG. 4).

Example 3

Construction of pDG268MCSΔneo-Pr$_{CryIIIA}$/cryIIIAstab/SAV

The introduction of an expression cassette, contained in pDG268MCS or a pDG268MCSΔ derivative, into the chromosome of a Bacillus cell must be confirmed by PCR analysis since there is no way of distinguishing whether the introduction into the chromosome is a result of a double (desired) versus a single cross-over event. In order to alleviate this problem, pDG268MCSΔneo-Pr$_{CryIIIA}$/cryIIIAstab/SAV was constructed to contain an antibiotic resistance marker conferring resistance to neomycin, outside of the amyE "front" and amyE "back" regions of homology. A double cross-over results in Cm$^r$, Neo$^s$ transformants whereas a single cross-over results in Cm$^r$, Neo$^r$ transformants allowing the identification of the desired double cross-over events by screening for drug resistances rather than PCR.

pDG268MCSΔneo-Pr$_{CryIIIA}$/cryIIIAstab/SAV was constructed first by digesting pDG268MCAΔ-Pr$_{CryIIIA}$/cryIIIAstab/SAV of Example 2 with BalI and treating with calf intestinal alkaline phosphatase. Plasmid pBEST501 (Itaya et al., 1989, *Nucleic Acids Research* 17: 4410) was digested with PstI and NotI, treated with T4 DNA poly-

```
            SfiI   ApaISmaIAatIIHindIIIClaI      BamHI
NotI
5'-AATTGGCCTTAAGGGCCCGGGACGTCAAGCTTATCGATGCGGATCCGCGGCCGC-3'    (SEQ ID NOs:1 and 2, respectively)
3'-CCGGAATTCCCGGGCCCTGCAGTTCGAATAGCTACGCCTAGGCGCCGGCGC-5'
```

Figure 3:
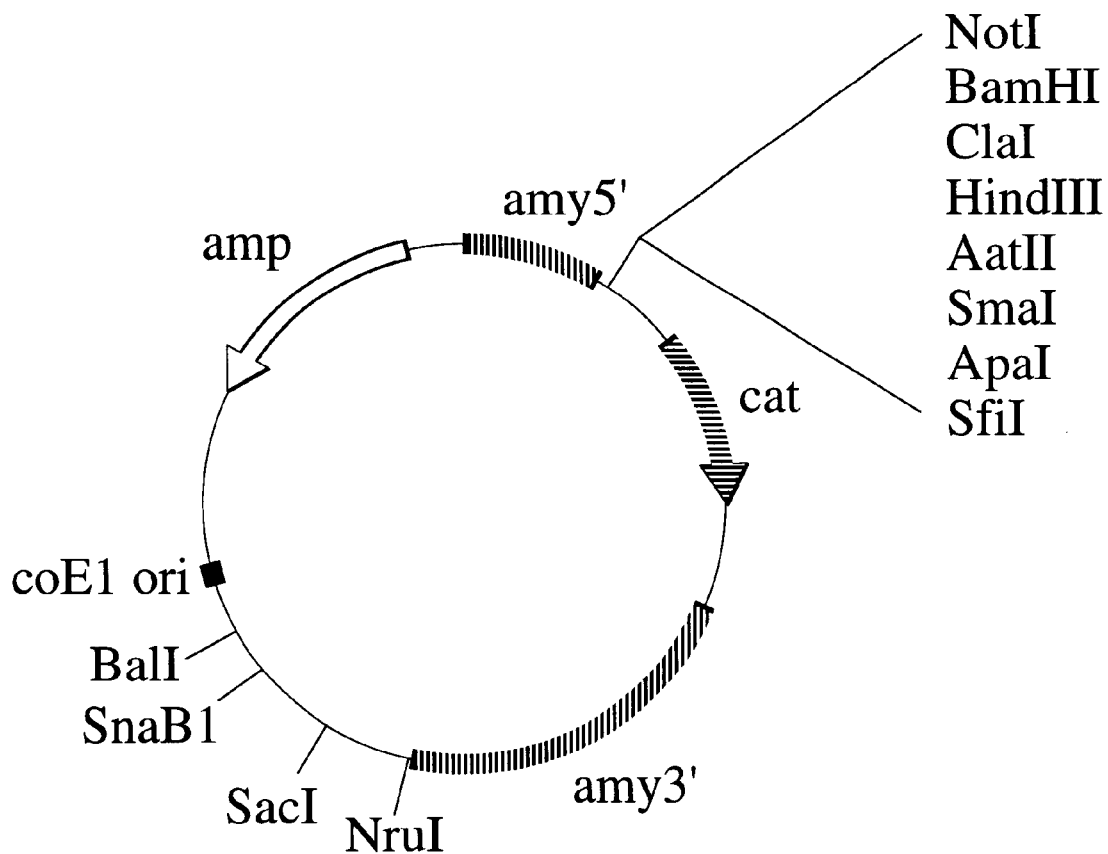
FIG. 3 shows a restriction map of pDG268MCS.
Figure 5:
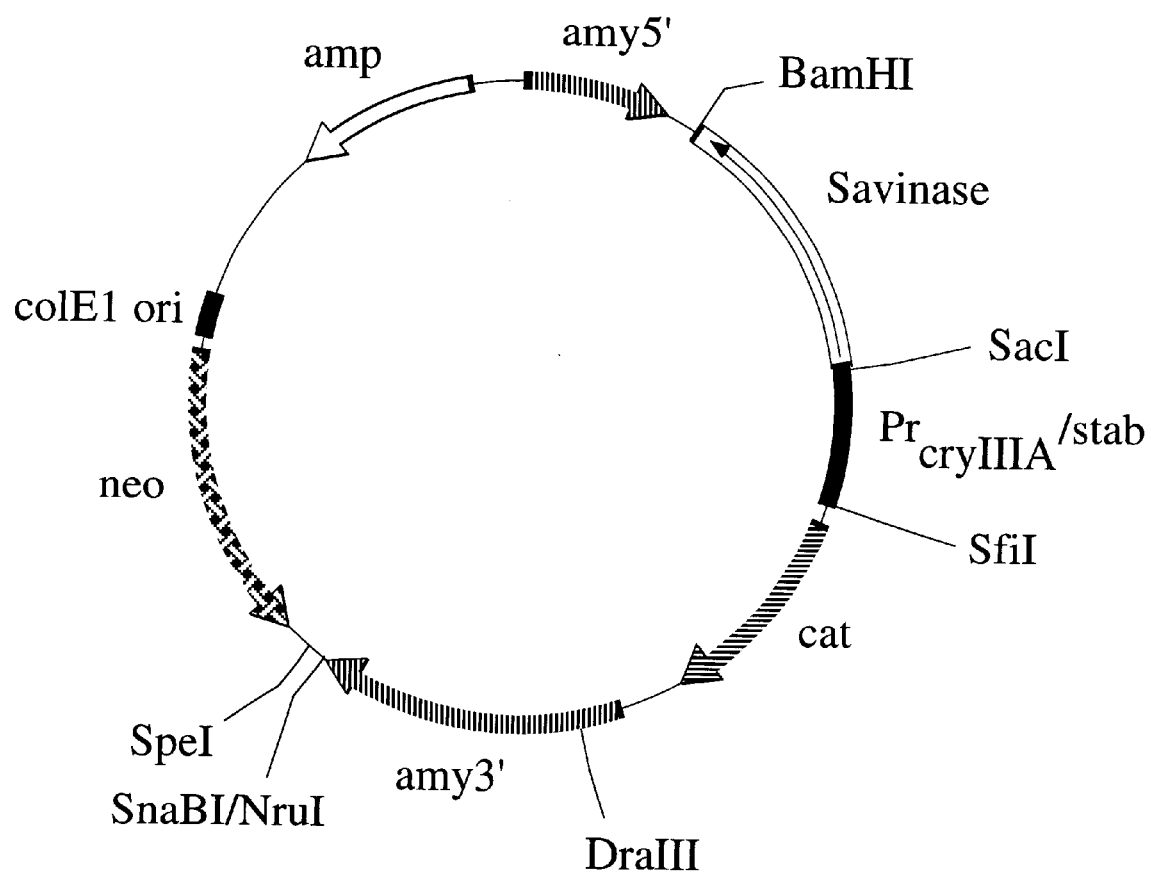
FIG. 5 shows a restriction map of pDG268MCSΔneo-Pr$_{cryIIIA}$/cryIIIAstab/SAV.

*E. coli* DH5α was transformed with the ligation mixture and ampicillin resistant transformants were selected on LB plates supplemented with 100 μg of ampicillin per ml. Plasmid DNA was purified according to Sambrook et al., 1989, supra, and digested with SfiI and NotI to identify plasmids which contained these sites and by implication, the polylinker shown above (pDG268 does not contain these two restriction sites). Several plasmids were identified which contained both restriction sites and in addition were approximately 3.0 kb smaller than pDG268 as a result of replacing the lacZ gene of pDG268 with the synthetic polylinker. One such plasmid was chosen and designated pDG268MCS (MCS refers to multiple cloning site) (FIG. 3).

merase I to generate blunt ends, and agarose gel purified as described in Example 1 to isolate a fragment harboring the neomycin resistance marker. The gel-purified fragment and BalI-digested plasmid were ligated together and transformed into *E. coli* DH5α. Ampicillin resistant transformants were selected on LB plates supplemented with 100 μg of ampicillin per ml. The selected transformants were patched onto LB plates supplemented with 50 μg of neomycin per ml to identify neomycin resistant transformants. Plasmid DNA was purified from a few of the neomycin resistant transformants as described in Example 1 and digested with BglII (cuts twice due to the additional BglII site introduced with the neomycin resistance marker) yielding two fragments in the 4 kb range and with BamHI (which is predicted to cut once downstream of the SAVINASE™ protease gene) yielding a fragment of approximately 8 kb. Such a plasmid was identified and designated pDG268MCSΔneo-Pr$_{cryIIIA}$/cryIIIAstab/SAV (FIG. 5).

Example 4

Construction of pHP13ampMCS pHP13-amp, a variant of pHP13 (Haima et al., 1987, *Molecular and General Genetics* 209: 335–342), was constructed by digesting pUC9 with AatII, blunting with Klenow fragment and deoxyribonucleotides, and then digesting with HindIII. The larger 2.2 kb fragment was gel-purified with a Qiaex kit (QIAGEN, Thousand Oaks, Calif.). pHP13 was digested with HpaI (which cuts within the erythromycin resistance gene), blunted, and then digested with HindIII. The larger 3.0 kb fragment released from pHP13 was then ligated to the 2.1 kb pUC9 fragment containing the pUC9 origin of replication and ampicillin resistance gene. The ligation mixture was transformed into *E. coli* DH5α. Ampicillin resistant transformants were selected on LB plates supplemented with 100 μg of ampicillin per ml. Plasmid DNA was purified from several transformants as described in Example 1. A plasmid designated pHP13amp was recovered from one of the transformants.

Plasmid pHP13amp was digested with EcoRI and HindIII and the pUC9 MCS was replaced with a new MCS created by annealing 100 pmol of the following polylinker in 50 mM NaCl, 10 mM Tris pH 7.5, and 1 mM EDTA, boiling for 5 minutes, and cooling slowly to room temperature over a 2 hour time period:

```
     SfiI  ApaISmaI        SacI  HindIIINotI   NcoI SalI
5'-AGCTAGGCCTTAAGGGCCCGGGACGTCGAGCTCAAGCTTGCGGCCGCCATGGTCGACG-3'    (SEQ ID NOs:3 and 4, repectively)
3'-TCCGGAATTCCCGGGCCCTGCAGCTCGAGTTCGAACGCCGGCGGTACCAGCTGCTTAA-5'
```

Figure 6:
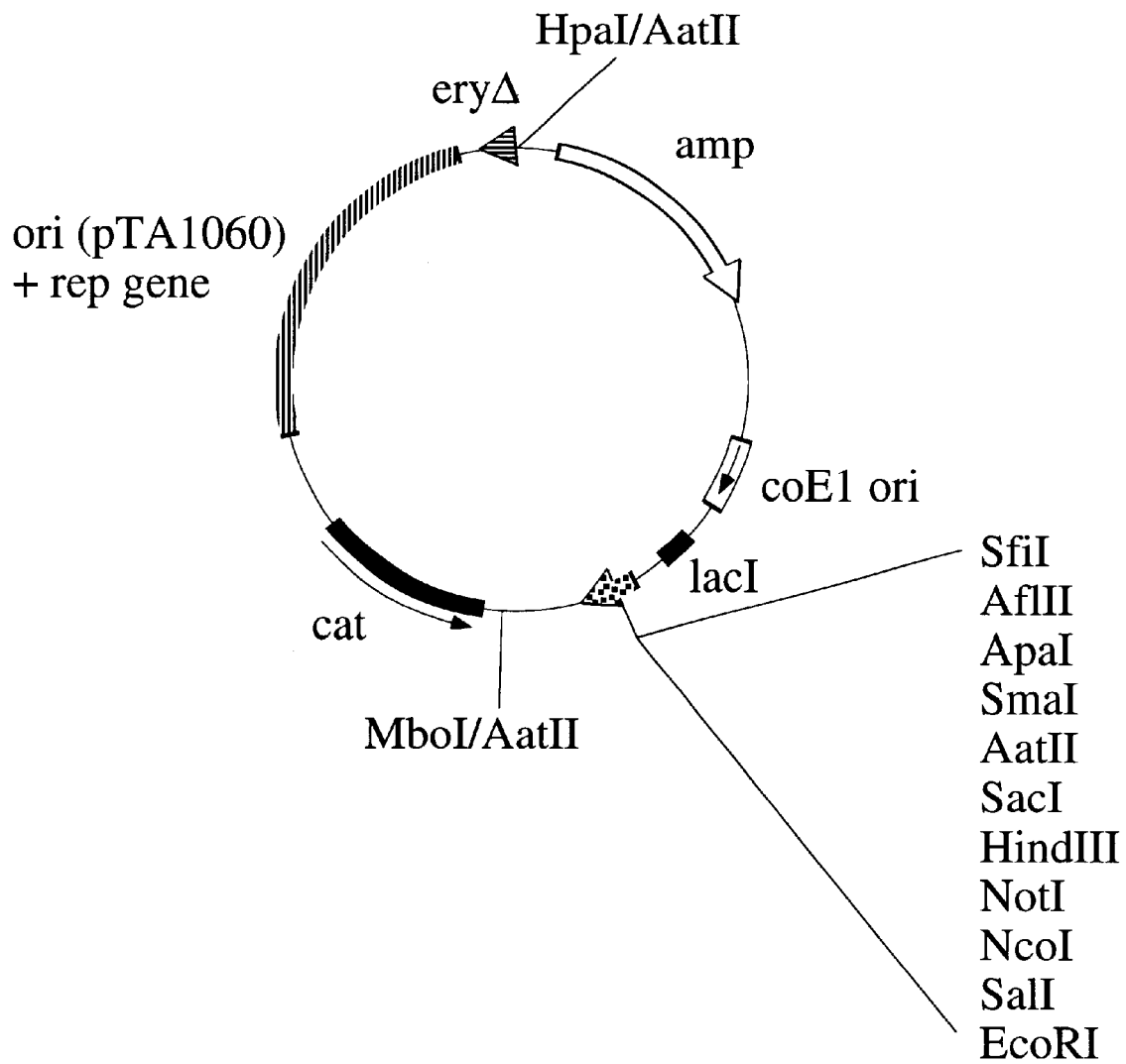
FIG. 6 shows a restriction map of pHP13amp-MCS.

*E. coli* DH5α was transformed with the ligation mix and ampicillin resistant transformants were selected on LB plates supplemented with 100 μg of ampicillin per ml. Plasmid DNA was purified from several transformants as described in Example 1 and digested with NotI and SacI. Plasmids which were cleaved with these enzymes contained the synthetic polylinker. One such plasmid was identified and designated pHP13amp-MCS (FIG. 6). This plasmid was further verified by DNA sequencing through the polylinker region. DNA sequencing was performed with an Applied Biosystems Model 373A Automated DNA Sequencer (Applied Biosystems, Inc., Foster City, Calif.) according to the manufacturer's instructions.

Example 5

Isolation of the SAVINASE™ Serine Protease Gene

Figure 7:
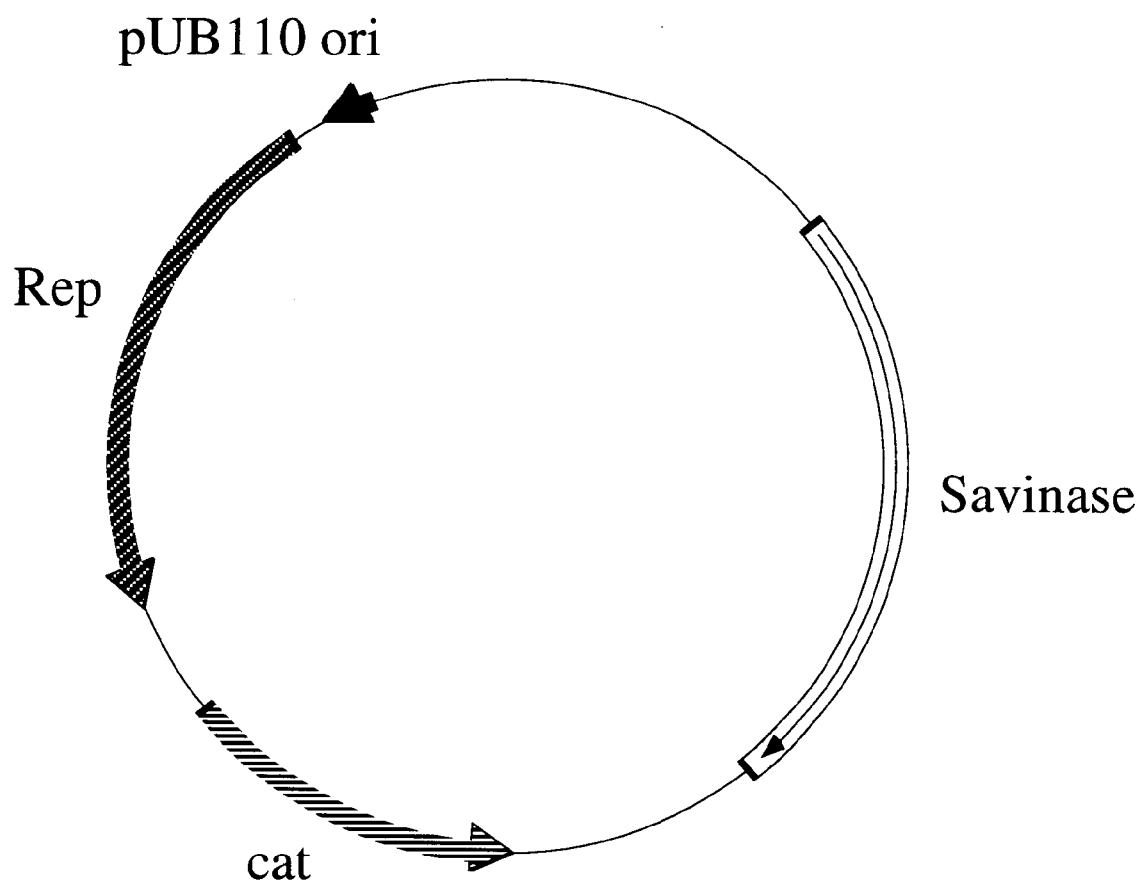
FIG. 7 shows a restriction map of pSX222.

The gene, which encodes a Bacillus serine protease (SAVINASE™, Novo Nordisk A/S, Bagsvxrd, Denmark), hereinafter referred to as the SAVINASE™ gene, was PCR-amplified using plasmid pSX222 (FIG. 7, U.S. Pat. No. 5,621,089) as template DNA and the following two primers (restriction sites are underlined):

```
      ApaI     SacI              (SEQ ID NO. 5)
5'-CTCCGGGCCCATCTGAGCTCTATAAAAATGAGGAGGG-3'

BamHI                      (SEQ ID NO. 6)
5'-CCTCGGATCCATACACAAAAAAACGCT-3'
```

The amplification reaction (100 μl) consisted of the following components: 50 ng of pSX222, 50 pmole of each primer, 1×Taq DNA polymerase Buffer (Boehringer Mannheim, Indianapolis, Ind.), 200 μM each of dATP, dTTP, dGTP, and dCTP, and 2.5 units of Taq DNA polymerase (Perkin-Elmer Corp., Branchburg, N.J.). The amplification conditions were one cycle at 95° C. for 3 minutes, 30 cycles each at 95° C. for 1 minute, 55° C. for 1 minute, and 72° C. for 1.5 minutes, and a final cycle at 72° C. for 5 minutes.

Figure 8:
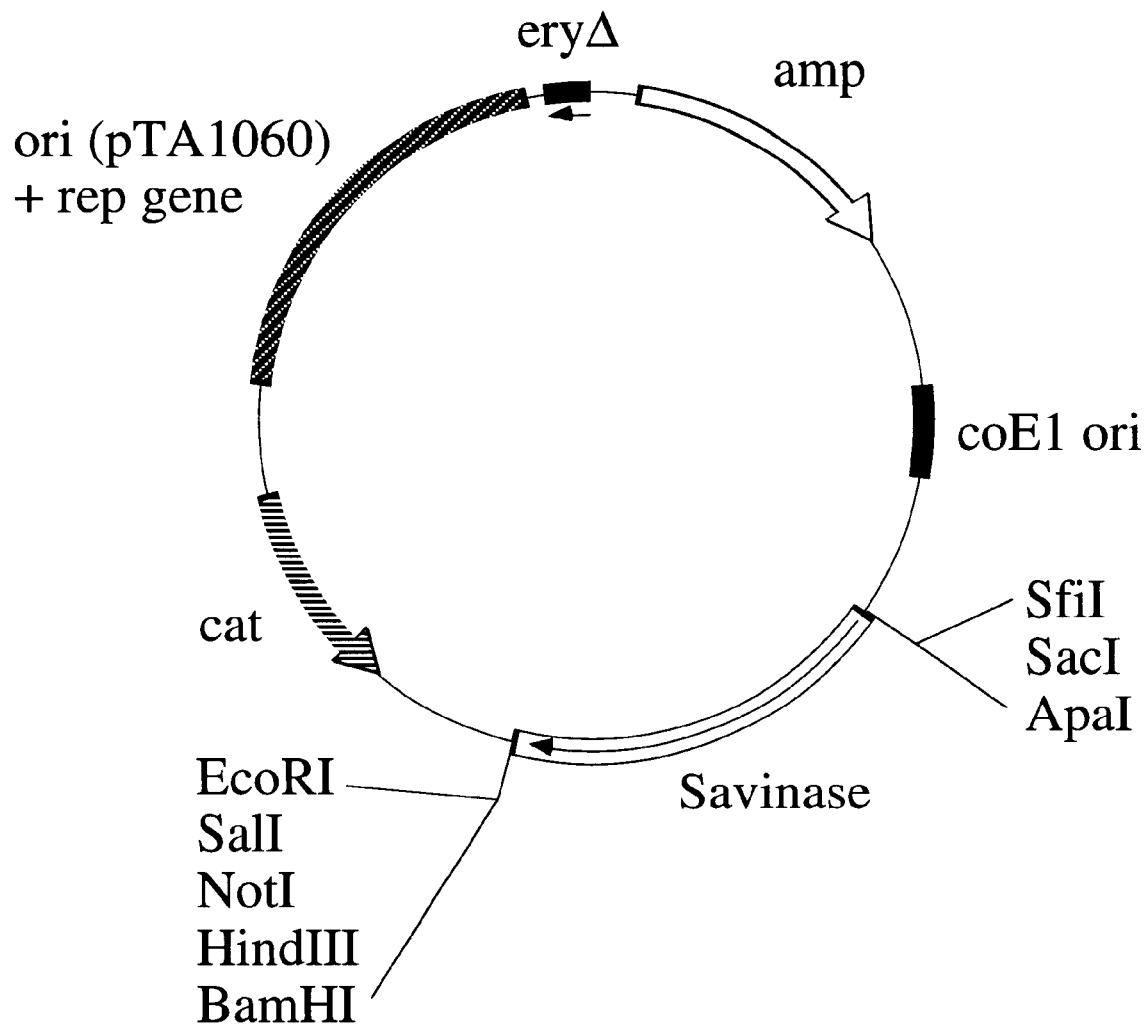
FIG. 8 shows a restriction map of pHP13amp-SAV.

The approximately 1230 bp PCR product was subcloned directly into the pCRII vector (Invitrogen, Carlsbad, Calif.) according to the manufacturer's instructions. The sequence of the gene was verified by DNA sequencing as described in Example 4 using gene-specific primers. Once verified, the plasmid was digested with BamHI, filled in with Klenow fragment, digested with ApaI, and the fragment harboring the SAVINAASE™ gene was then ligated into the ApaI, Ecl136II site of pHP13ampMCS. *E. coli* DH5α was transformed with this ligation mixture and ampicillin resistant transformnants were selected on LB plates supplemented with 100 μg of ampicillin per ml. A plasmid designated pHP13amp-SAV (FIG. 8) was isolated from one of the transformants and verified by DNA sequencing as described in Example 4 using construct-specific primers. The BamHI site was regenerated as a result of this ligation.

Example 6

Construction of an amyL Promoter-SAVINAASE™ Gene Expression Cassette

The promoter of the amyL gene, which encodes a *Bacillus licheniformis* alpha-amylase (TERMAMYL™, Novo Nordisk A/S, Bagsv.Trd, Denmark), described in U.S. Pat. No. 5,698,415 was PCR-amplified using plasmid pPL1759 (U.S. Pat. No. 5,698,415) as template DNA, the following two primers (restriction sites are underlined), and GENEAMP® XL PCR Kit (Perkin-Elmer Corp., Branchburg, N.J.) according to the manufacturer's instructions:

```
      SfiI                       (SEQ ID NO. 7)
5'-CCAGGCCTTAAGGGCCGCATGCGTCCTTCTTTGTGCT-3'

SacI                       (SEQ ID NO. 8)
5'-CCAGAGCTCCTTTCAATGTGTAACATATGA-3'
```

The amplification reaction (100 μl) consisted of the following components: 50 ng of pPL1759, 50 pmole of each primer, 1×Taq polymerase buffer, 2.5 μM each of dATP, dTTP, dGTP, and dCTP, and 1.0 unit of Taq polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

The approximately 620 bp PCR product containing the amyL promoter was ligated with Ecl136II-digested pUC118.

Figure 9:
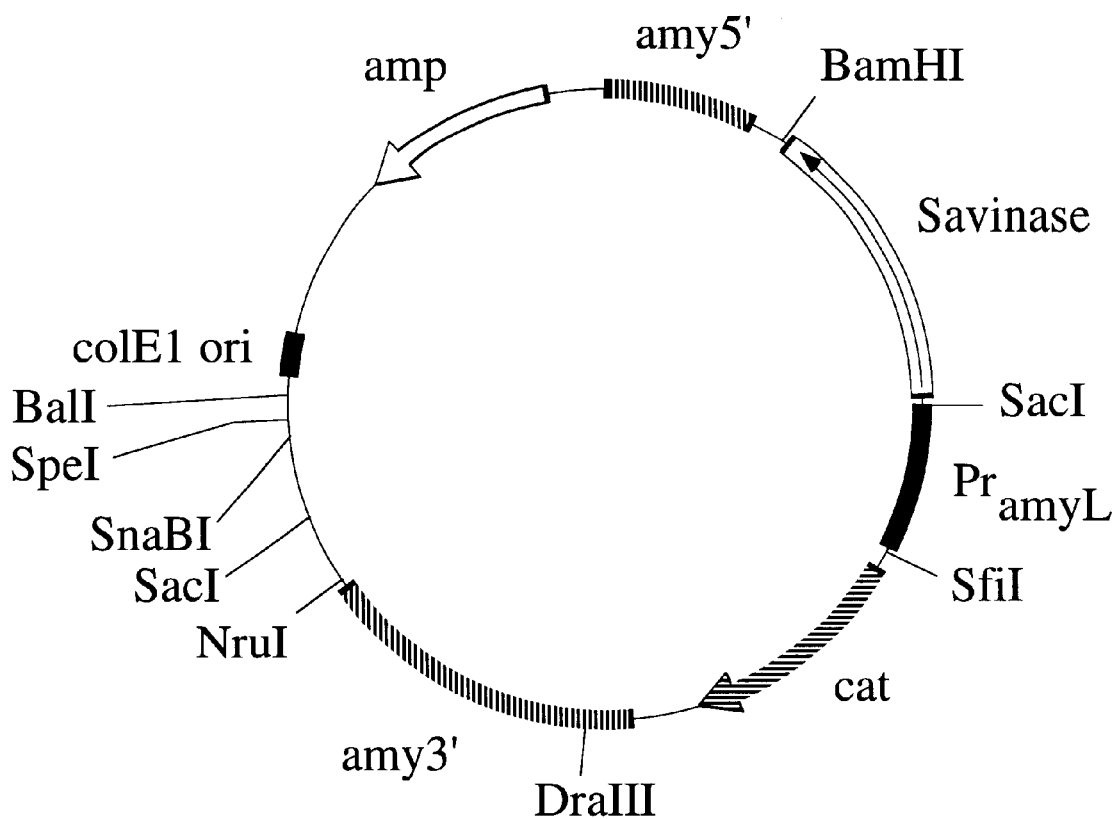
FIG. 9 shows a restriction map of pDG268MCS-Pr$_{amyL}$/SAV.

E. coli DH5α was transformed with this ligation mixture and ampicillin resistant transformants were selected on LB plates supplemented with 100 μg of ampicillin per ml. A plasmid designated pUC118-Pr$_{amyL}$ was purified from an ampicillin resistant transformant that appeared white in the presence of 5-bromo4-chloro-3-inodlyl-â-D-galactopyranoside (Sigma, St. Louis, Mo.) and verified by DNA sequencing as described in Example 4, using M13/pUC sequencing primers and amyL-specific primers.

pHP13amp-SAV of Example 5 was digested with SfiI and SacI and purified by gel electrophoresis, as described in Example 1. The approximately 620 bp SfiI-SacI fragment of pUC118-Pr$_{amyL}$ bearing the amyL promoter was isolated by gel electrophoresis, as described in Example 1, and ligated to SfiI/SacI-digested pHP13amp-SAV. E. coli DH5α was transformed with this ligation mixture and ampicillin resistant transformants were selected on LB plates supplemented with 100 μg of ampicillin per ml. A plasmid designated pHP13amp-Pr$_{amyL}$/SAV was purified from one of the ampicillin resistant transformants.

pHP13amp-Pr$_{amyL}$/SAV was digested with SfiI and BamHI and the approximately 1840 bp fragment bearing the Pr$_{amyL}$/SAV cassette was purified as described in Example 1. pDG268MCS was digested with SfiI and BamHI, purified as described in Example 1, and ligated with the Pr$_{amyL}$/SAV SfiI/BamHI fragment. E. coli DH5α was transformed with this ligation mixture and ampicillin resistant transformants were selected on LB plates supplemented with 100 μg of ampicillin per ml. A plasmid designated pDG268MCS-Pr$_{amyL}$/SAV (FIG. 9) was purified from one of the ampicillin resistant transformants.

Example 7

Construction of an amyQ Promoter-SAVINAASE™ Gene Expression Cassette

The promoter of the amyQ gene which encodes a Bacillus amyloliquefaciens alpha-amylase (BANTM, Novo Nordisk A/S, Bagsvxrd, Denmark) was PCR-amplified using plasmid pSX222 as template DNA and the following primers (restriction sites are underlined):

```
        SfiI                         (SEQ ID NO. 9)
5'-TTTGGCCTTAAGGGCCTGCAATCGATTGTTTGAGAAAAGAAG-3'

SacI                         (SEQ ID NO. 10)
5'-TTTGAGCTCCATTTTCTTATACAAATTATATTTTACATATCAG-3'
```

The amplification reaction (100 μl) consisted of the following components: 50 ng of pSX222, 50 pmole of each primer, 1×Taq DNA polymerase buffer, 200 μM each of dATP, dTTP, dGTP, and dCTP, and 2.5 units of Taq DNA polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

Figure 10:
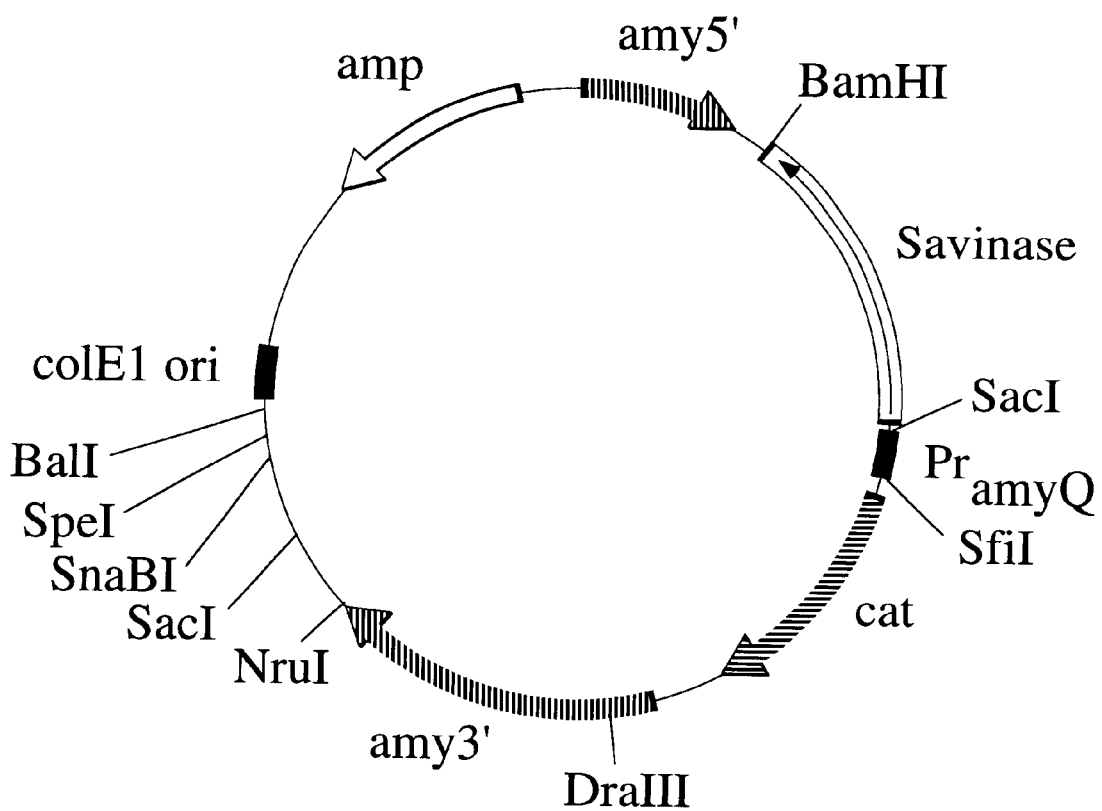
FIG. 10 shows a restriction map of pDG268MCS-Pr$_{amyQ}$/SAV.

The approximately 185 bp PCR product was subcloned directly into the pCRII vector according to the manufacturer's instructions and verified by DNA sequencing as described in Example 4 yielding pCRII-Pr$_{amyQ}$. The approximately 185 bp SfiI-SacI fragment of pCRII-Pr$_{amyQ}$ bearing the amyQ promoter was isolated by gel electrophoresis, as described in Example 1, and ligated to SfiI/SacI-digested pHP13amp-SAV (Example 5). E. coli DH5α was transformed with this ligation mixture and ampicillin resistant transformants were selected on LB plates supplemented with 100 μg of ampicillin per ml. A plasmid designated pHP13amp-Pr$_{amyQ}$/SAV was purified from one of the ampicillin resistant transformants.

pHP13amp-Pr$_{amyQ}$/SAV was digested with SfiI and BamHI, and the approximately 1400 bp fragment bearing the Pr$_{amyQ}$/SAV expression cassette was purified as described in Example 1. The SfiI-BamHI fragment was then ligated into SfiI-BamHI digested pDG268MCS (Example 6). E. coli DH5α was transformed with this ligation mixture and ampicillin resistant transformants were selected on LB plates supplemented with 100 μg of ampicillin per ml. A plasmid designated pDG268MCS-Pr$_{amyQ}$/SAV (FIG. 10) was purified from one of the ampicillin resistant transformants.

Example 8

Construction of pUC18-Pr$_{cryIIIA}$/cryIIIAstab/cryIIIA

The promoter of the cryIIA gene which encodes a Bacillus thuringiensis subsp. tenebrionis coleopteran crystal protein CryIIIA was PCR amplified from chromosomal DNA isolated according to Pitcher et al., 1989, Letters in Applied Microbiology 8: 151–156 from the Bacillus thuringiensis subsp. tenebrionis strain NB125 described in WO 95/02695 using the following primers:

```
        SmaI                         (SEQ ID NO. 11)
5'-GAGACCCGGGAGCTTTCAGTGAAGTACGTG-3'

5'-GGGGCGTTACAATTCAAAG-3'            (SEQ ID NO. 12)
```

The amplification reaction (100 μl) consisted of the following components: 50 ng of NB125 chromosomal DNA, 50 pmole of each primer, 1×Pyfu polymerase buffer (Stratagene Cloning Systems, La Jolla, Calif.), 200 μM each of dATP, dTTP, dGTP, and dCTP, and 1.0 unit of Pfu polymerase (Stratagene Cloning Systems, La Jolla, Calif.). The amplification conditions were one cycle at 95° C. for 3 minutes; 30 cycles each at 95° C. for 1 minute, 50° C. for 1 minute, and 72° C. for 1.5 minutes; and a final cycle at 72° C. for 5 minutes. The approximately 1000 bp PCR product was digested with SmaI and HindIII and ligated into the SmaI/HindIII site of pUC18. E. coli DH5α was transformed with this ligation mixture and ampicillin resistant transformants were selected on LB plates supplemented with 100 μg of ampicillin per ml. A plasmid designated pUC18-Pr$_{cryIIIA}$ was isolated from one of the ampicillin resistant transformants.

Figure 11:
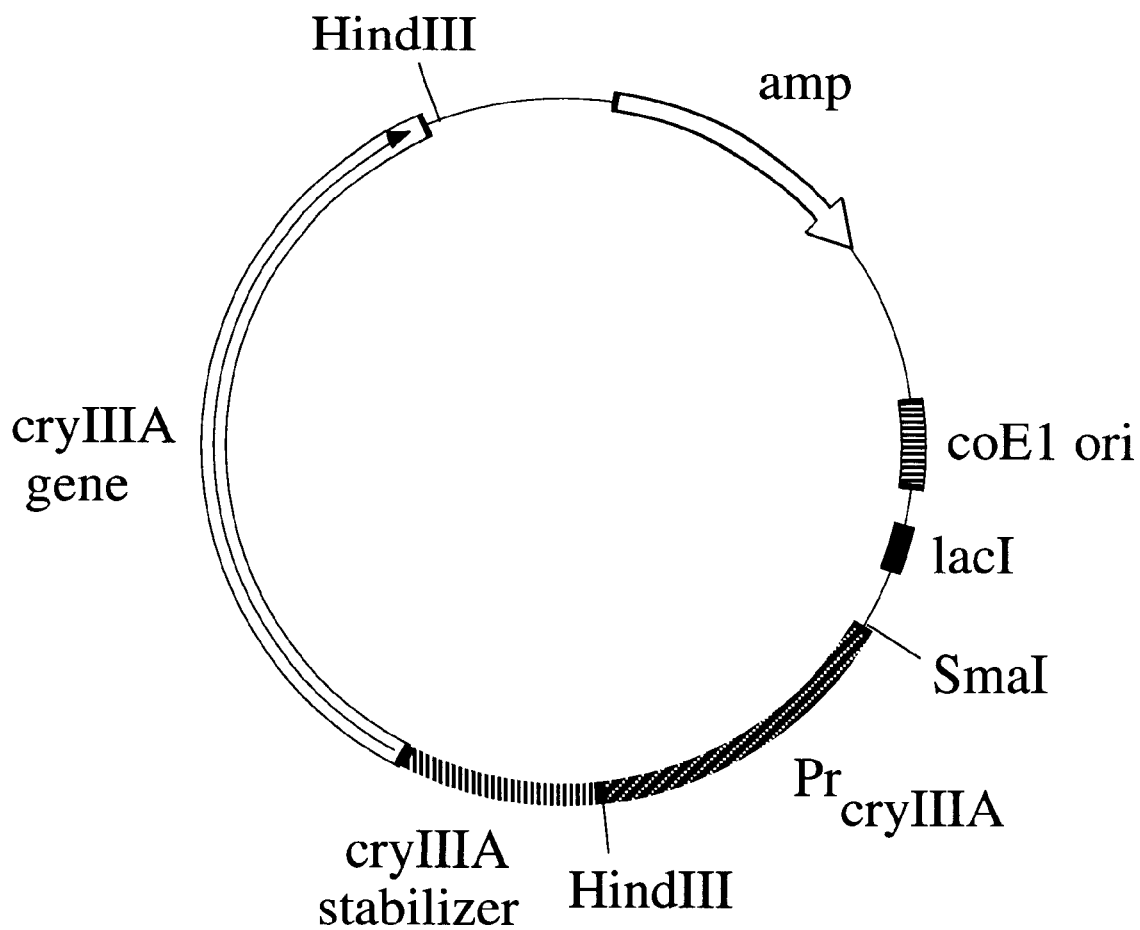
FIG. 11 shows a restriction map of pUC18-Pr$_{cryIIIA}$/cryIIIAstab/cryIIIA.

Plasmid pUC118-cryIIIA (WO 95/02695) was digested with HindIII and the approximately 3000 bp HindIII fragment harboring the cryIIIA gene and mRNA stabilizing sequence was gel-purified as described in Example 1. This fragment was ligated into the HindIII site of pUC18-Pr$_{cryIIIA}$. E. coli DH5α was transformed with this ligation mixture and ampicillin resistant transformants were selected on LB plates supplemented with 100 μg of ampicillin per ml. A plasmid designated pUC18-Pr$_{cryIIIA}$/cryIIIAstab/cryIIIA (FIG. 11) was isolated from one of the ampicillin resistant transformants. The correct orientation of the fragment was confirmed by digesting the plasmid with EcoRI.

Example 9

Construction of a cryIIIA Promoter-cryIIIA mRNA Stabilizer-SAVINASE™ Gene Expression Cassette The promoter and cryIIIA mRNA stabilizing sequence of the cryIIIA gene were PCR amplified using plasmid pUC18-

Pr$_{cryIIIA}$/cryIIIAstab/cryIIIA of Example 8 as DNA template and the two primers (restriction sites are underlined) described below:

```
    ApaI
5'-                              (SEQ ID NO. 13)
GGGCCCTCGAAACGTAAGATGAAACCT-3'

SacI
5'-                              (SEQ ID NO. 14)
GAGCTCCATAATACATAATTTTCAAACTG-3'
```

The amplification reaction (100 1 μl) consisted of the following components: 50 ng of pUC18-Pr$_{cryIIIA}$/cryIIIAstab, 50 pmole of each primer, 1×Taq polymerase buffer, 200 μM each of dATP, dTTP, dGTP, and dCTP, and 1.0 unit of Taq polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

The approximately 630 bp PCR product was cloned in the pCRII vector according to the manufacturer's instructions, yielding plasmid pCRII-Pr$_{cryIIIA}$/cryIIIAstab, which was verified by DNA sequencing as described in Example 4, using M13 sequencing primers and cryIIIA-specific primers.

The approximately 630 bp SfiI-SacI fragment of pCRII-Pr$_{cryIIIA}$/cryIIIAstab bearing the cryIIIA promoter (Pr$_{cryIIIA}$) with mRNA stabilizer sequence was isolated by gel electrophoresis, as described in Example 1, and ligated to SfiI/SacI-digested pHP13amp-SAV (Example 5). E. coli DH5α was transformed with this ligation mixture and ampicillin resistant transformants were selected on LB plates supplemented with 100 μg of ampicillin per ml. A plasmid designated pDG268MCS-Pr$_{cryIIIA}$/cryIIIAstab/SAV (FIG. 12) was purified from one of the ampicillin resistant transformants.

Example 10

Construction of a cryIIIA Promoter-SAVINAASE™ Gene Expression Cassette pDG268Δneo-Pr$_{cryIIIA}$/SAV was constructed as follows. A fragment of approximately 1640 bp of pDG268MCSΔneo-Pr$_{cryIIIA}$/cryIIIAstab/SAV of Example 3 ranging from the DraIII site to 6 nucleotides downstream of the cryIIIA transcription start site was PCR-amplified using plasmid pDG268MCSΔneo-Pr$_{cryIIIA}$/cryIIIAstab/SAV as DNA template and the following two primers (restriction sites are underlined):

```
        DraIII
5'-CAGCCATCACATTGTGAAATC-3'      (SEQ ID NO. 15)

SacI
5'-GAGCTCTATCTTTAATTAAGCTT-3'    (SEQ ID NO. 16)
```

Figure 13:
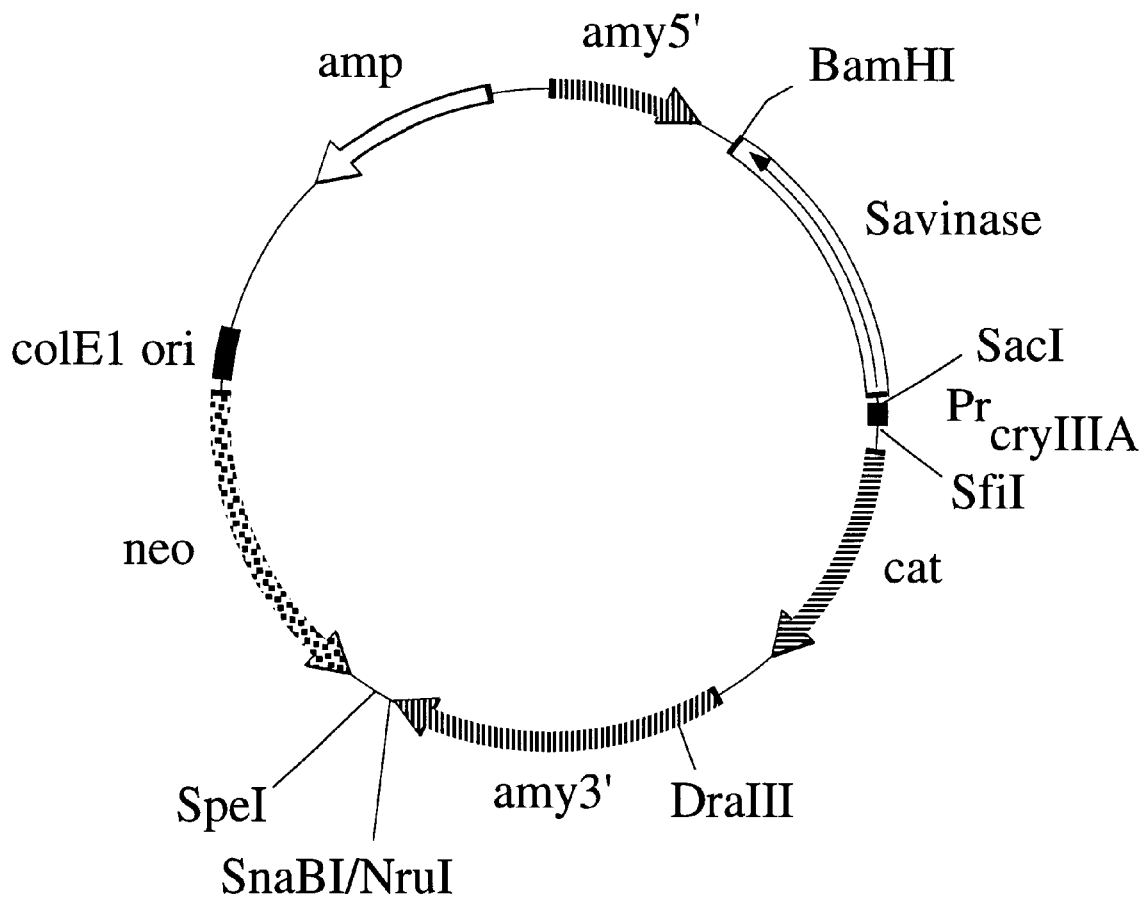
FIG. 13 shows a restriction map of pDG268MCSΔneo-Pr$_{cryIIIA}$/SAV.

The amplification reaction (50 μl) consisted of the following components: 50 ng of pDG268MCSΔneo-Pr$_{cryIIIA}$/cryIIIAstab/SAV, 50 pmole of each primer, 1×Taq polymerase Buffer, 200 μM each of dATP, dTTP, dGTP, and dCTP, and 1.25 unit of Amplitaq® Gold DNA polymerase (Perkin-Elmer Corporation, Branchburg, N.J.). The amplification conditions were one cycle at 95° C. for 9 minutes; 30 cycles of 95° C. for 1 minute, 55° C. for 1 minute, and 72° C. for 1.5 minutes; and a final cycle at 72° C. for 3 minutes. The PCR product was cloned directly into pCR2.1 using the TOPO-TA Cloning Kit (Invitrogen, Carlsbad, Calif.) according to the manufacturer's instructions yielding pCR2.1-DraIII/Pr$_{cryIIIA}$, which was verified by DNA sequencing as described in Example 4.

pDG268MCSΔneo- Pr$_{amyL}$/Pr$_{cryIIIA}$/cryIIIAstab/SAV of Example 12 was digested with DraIII and SacI to remove the Pr$_{amyL}$/Pr$_{cryIIIA}$/cryIIIAstab tandem promoter and part of the vector, and the approximately 6440 bp vector fragment was isolated by gel electrophoresis, as described in Example 1. The approximately 1640 bp DraIII/SacI fragment of pCR2.1-DraIII/Pr$_{cryIIIA}$ was isolated and ligated with the DraIIISacI-cut vector. E. coli DH5α was transformed with this ligation mixture and ampicillin resistant transformants were selected on LB plates supplemented with 100 μg of ampicillin per ml. A plasmid designated pDG268MCSΔneo-Pr$_{cryIIIA}$/SAV (FIG. 13) was purified from one of the ampicillin resistant transformants.

Example 11

Construction of an amyL Promoter-cryIIIA mRNA Stabilizer-SAVINAASE™ Gene Expression Cassette The cryIIIA mRNA stabilizer sequence was PCR-amplified using plasmid pUC18-Pr$_{cryIIIA}$/cryIIIAstab/cryIIIA of Example 8 as DNA template and the following two primers (SacI restriction sites are underlined):

```
5'-GAGCTCGAACTTGTTCATGTGAA-3'    (SEQ ID NO. 17)
5'-GAGCTCATAATACATAATTTTCA-3'    (SEQ ID NO. 18)
```

The amplification reaction (100 μl) consisted of the following components: 50 ng of pUC18-Pr$_{cryIIIA}$/cryIIIAstab/cryIIIA, 50 pmole of each primer, 1×Taq DNA polymerase Buffer, 200 μM each of dATP, dTTP, dGTP, and dCTP, and 2.5 units of Taq DNA polymerase. The amplification conditions were one cycle at 95° C. for 3 minutes, 30 cycles each at 95° C. for 1 minute, 55° C. for 1 minute, and 72° C. for 1.5 minutes, and a final cycle at 72° C. for 5 minutes. The approximately 360 bp PCR product was subcloned directly into the pCRII vector according to the manufacturer's instructions and confirmed by DNA sequencing, as described in Example 4, using construct specific primers.

Figure 14:
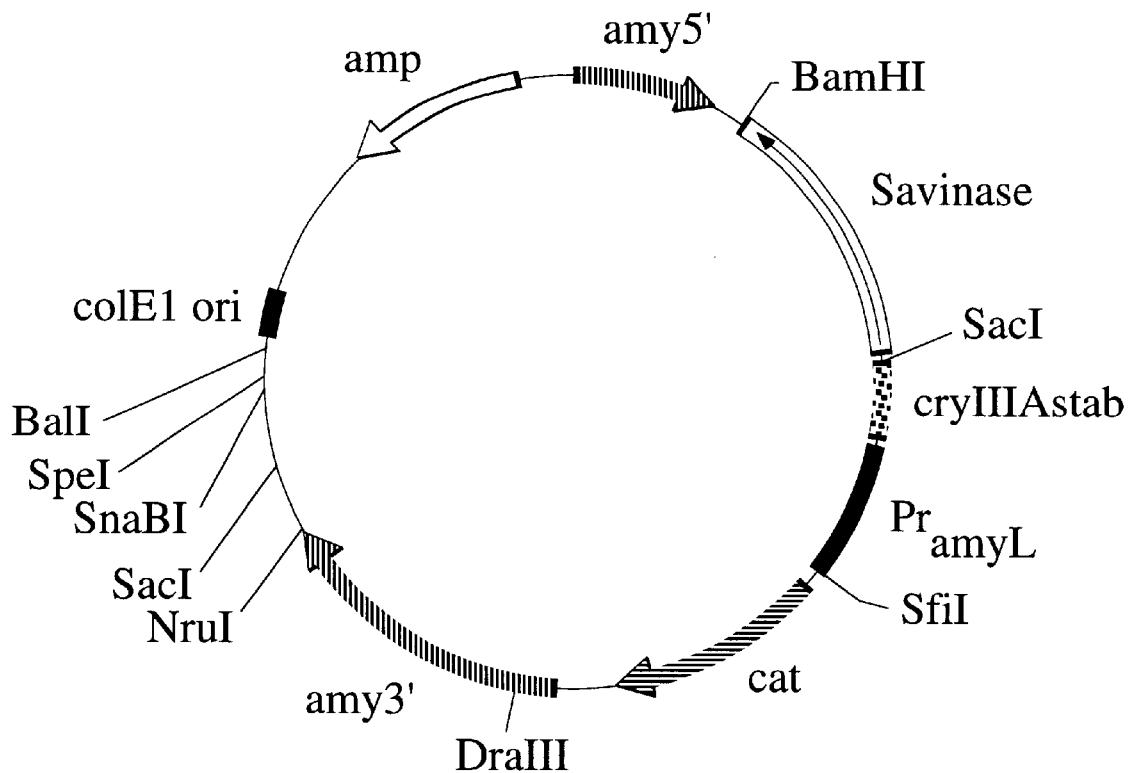
FIG. 14 shows a restriction map of pDG268MCS-Pr$_{amyL}$cryIIIAstab/SAV.

The resulting plasmid designated pCRII-cryIIIAstab was digested with SacI and the fragment harboring the cryIIIA mRNA stabilizer sequence was purified by agarose gel electrophoresis as described in Example 1. Plasmid pHP13amp-Pr$_{amyL}$/SAV of Example 6 was digested with SacI and treated with calf intestine alkaline phosphatase (CIP) to remove the 5' phosphate groups. The purified fragment containing the stabilizer sequence and the CIP-treated plasmid were then ligated together. E. coli DH5α cells were transformed with this ligation mixture and ampicillin resistant transformants were selected on LB plates supplemented with 100 μg of ampicillin per ml. Plasmid DNA was isolated from several transformants and digested with SacI to identify those which contained the mRNA stabilizer sequence. Once these were identified, the orientation of the fragment was determined by digesting the plasmid DNA with XmnI. A plasmid containing the cryIIIA stabilizing sequence in the correct orientation was identified and designated pHP13amp-Pr$_{amyL}$/cryIIIAstab/SAV.

pHP13amp-Pr$_{amyL}$/cryIIIAstab/SAV was digested with SfiI and BamHI and the fragment harboring the expression cassette was ligated into the SfiI-BamHI site of pDG268-MCS to produce pDG268MCS-Pr$_{amyL}$/cryIIIAstab/SAV (FIG. 14).

Example 12

Construction of a Tandem amyL-cryIIIA Promoter-cryIIIA mRNA Stabilizer-SAVINAASE™ Gene Expression Cassette

Plasmid pDG268MCSΔneo-Pr$_{cryIIIA}$/cryIIIAstab/SAV of Example 3 was digested with SfiI, blunt-ended with T4 polymerase I, and then digested with DraIII. The digest was separated by agarose gel electrophoresis and the vector fragment of approximately 7010 bp was excised from the gel and the DNA extracted as described in Example 1.

pDG268MCS-Pr$_{amyL}$/SAV of Example 6 was digested with Ecl136II and DraIII. The digest was separated by agarose gel electrophoresis, the promoter fragment of approximately 2150 bp was excised from the gel, and the DNA was extracted as described in Example 1.

Figure 15:
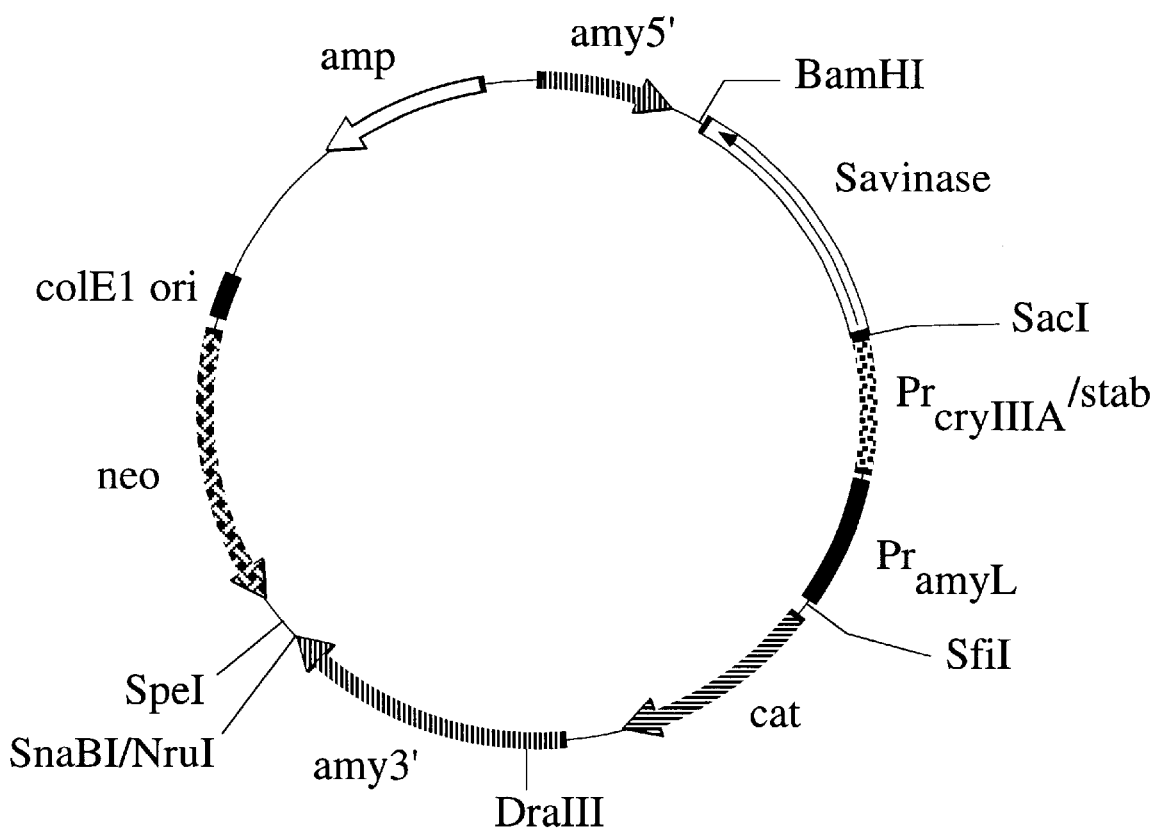
FIG. 15 shows a restriction map of pDG268MCSΔneo-Pr$_{amyL}$/Pr$_{cryIIIA}$/cryIIIAstab/SAV.

The purified DNAs were ligated together and transformed into E. coli DH5α. Ampicillin resistant transformants were selected on LB plates supplemented with 100 μg of ampicillin per ml. A plasmid designated pDG268MCSΔneo-Pr$_{amyL}$/Pr$_{cryIIIA}$/cryIIIAstab/SAV (FIG. 15) was isolated from one of the transformants and verified by digesting with NcoI followed by agarose gel electrophoresis.

Example 13

Figure 16:
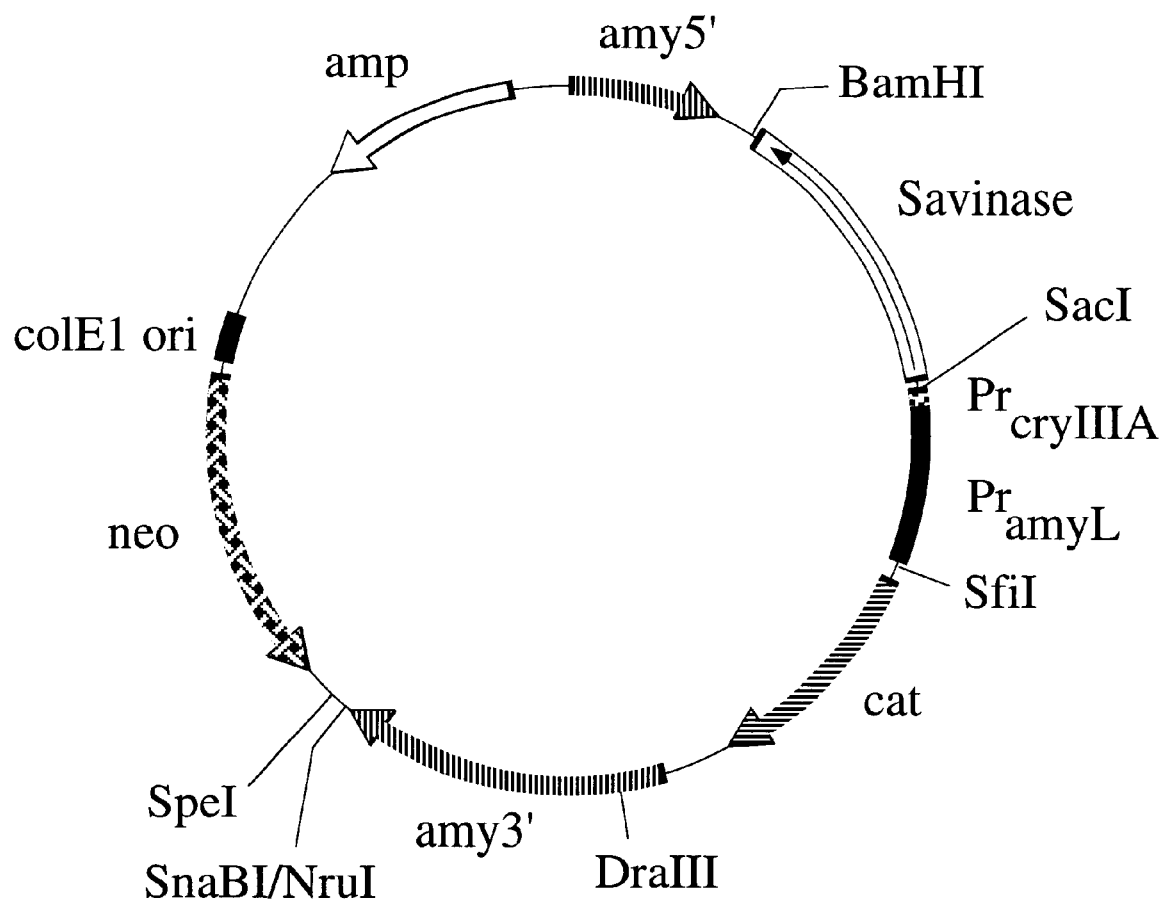
FIG. 16 shows a restriction map of pDG268MCSΔneo-Pr$_{amyL}$/Pr$_{cryIIIA}$/SAV.

Construction of a Tandem amyL-cryIIIA Promoter-SAVINAASE™ Gene Expression Cassette pDG268MCSΔneo-Pr$_{cryIIIA}$/SAV of Example 10 was digested with PacI and DraIII, and the approximately 6450 bp vector fragment was isolated by gel electrophoresis, as described in Example 1. The approximately 2230 bp PacI-DraIII fragment of pDG268MCSΔneo-Pr$_{amyL}$/Pr$_{cryIIIA}$/cryIIIAstab/SAV of Example 12 bearing Pr$_{amyL}$ and Pr$_{cryIIIA}$ was isolated by gel electrophoresis, as described in Example 1, and ligated with the vector fragment. E. coli DH5α was transformed with this ligation mixture and ampicillin resistant transformants were selected on LB plates supplemented with 100 μg of ampicillin per ml. A plasmid designated pDG268MCSΔneo-Pr$_{amyL}$/Pr$_{cryIIIA}$/SAV (FIG. 16) was purified from one of the ampicillin resistant transformants.

Example 14

Construction of an amyQ Promoter-cryIIIA Stabilizer-SAVINAASE™ Gene Expression Cassette pDG268MCS-Pr$_{amyQ}$/SAV of Example 7 was digested with SfiI and BamHI and the approximately 1400 bp bearing the Pr$_{amyQ}$/SAV cassette was isolated by gel electrophoresis, as described in Example 1. pDG268MCSΔneo-Pr$_{cryIIIA}$/cryIIIAstab/SAV of Example 3 was digested with SfiI and BamHI and the approximately 6780 bp vector fragment was isolated by gel electrophoresis, as described in Example 1. The purified fragments were ligated together, E. coli DH5α was transformed with the ligation mixture, and ampicillin resistant transformants were selected on LB plates supplemented with 100 μg of ampicillin per ml. A plasmid designated pDG268MCSΔneo-Pr$_{amyQ}$/SAV was purified from one of the ampicillin resistant transformants and verified by digestion with NcoI followed by gel electrophoresis.

pDG268MCSΔneo-Pr$_{amyQ}$/cryIIIAstab/SAV was constructed first by digesting pDG268MCSΔneo-Pr$_{amyQ}$/SAV with SacI and treating with calf intestine alkaline phosphatase to remove the 5' phosphate groups. The approximately 360 bp SacI fragment of pDG268MCS-Pr$_{amyL}$/cryIIIAstab/SAV of Example 11 bearing the cryIIIA leader was gel-purified as described in Example 1 and ligated with SacI-cut, dephosphorylated pDG268MCSΔneo-Pr$_{amyQ}$/SAV.

Figure 17:
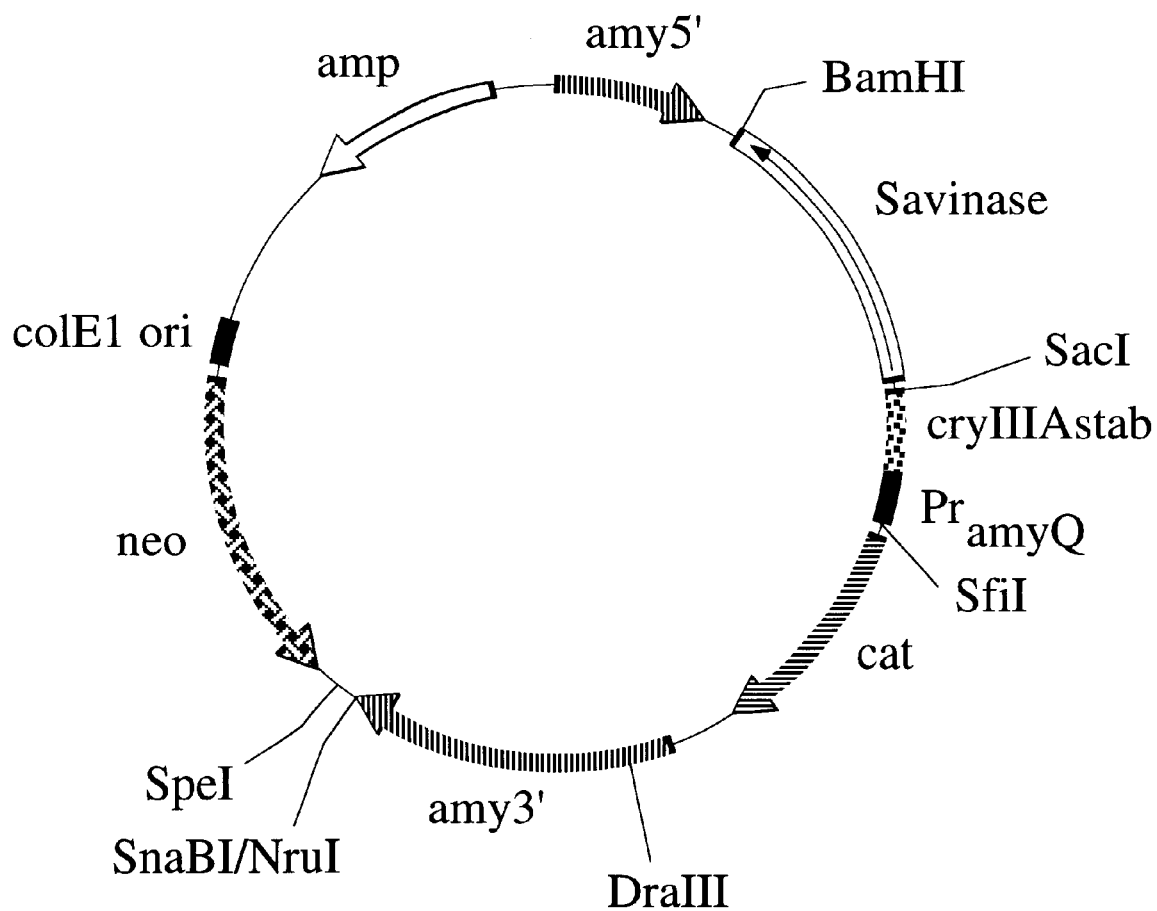
FIG. 17 shows a restriction map of pDG268MCSΔneo-Pr$_{amyQ}$/cryIIIAstab/SAV.

E. coli DH5α was transformed with this ligation mixture and ampicillin resistant transformants were selected on LB plates supplemented with 100 μg of ampicillin per ml. Plasmid DNA was isolated from several transformants and digested with SacI to identify those which contained the stabilizer sequence. Once these were identified, the orientation of the fragment was determined by digesting the plasmid DNA with XmnI. A plasmid containing the cryIIIA mRNA stabilizing sequence in the correct orientation was identified and designated pDG268MCSΔneo-Pr$_{amyQ}$/cryIIIAstab/SAV (FIG. 17).

Example 15

Construction of a Tandem amyQ-cryIIIA Promoter-cryIIIA mRNA Stabilizer-SAVINASET Gene Expression Cassette

Plasmid pDG268MCS-Pr$_{cryIIIA}$/cryIIIAstab/SAV of Example 9 was digested with SfiI, blunt-ended with T4 polymerase I, and then digested with DraIII. The digest was subjected to agarose gel electrophoresis and the vector fragment of approximately 6360 bp was excised from the gel and the DNA extracted as described in Example 1.

Plasmid pDG268MCS-Pr$_{amyQ}$/SAV of Example 7 was digested with SacI, blunt-ended with T4 DNA polymerase I, digested with DraIII. The digest was subjected to agarose gel electrophoresis and the promoter fragment of approximately 1710 bp was excised from the gel and the DNA extracted as described in Example 1.

Figure 18:
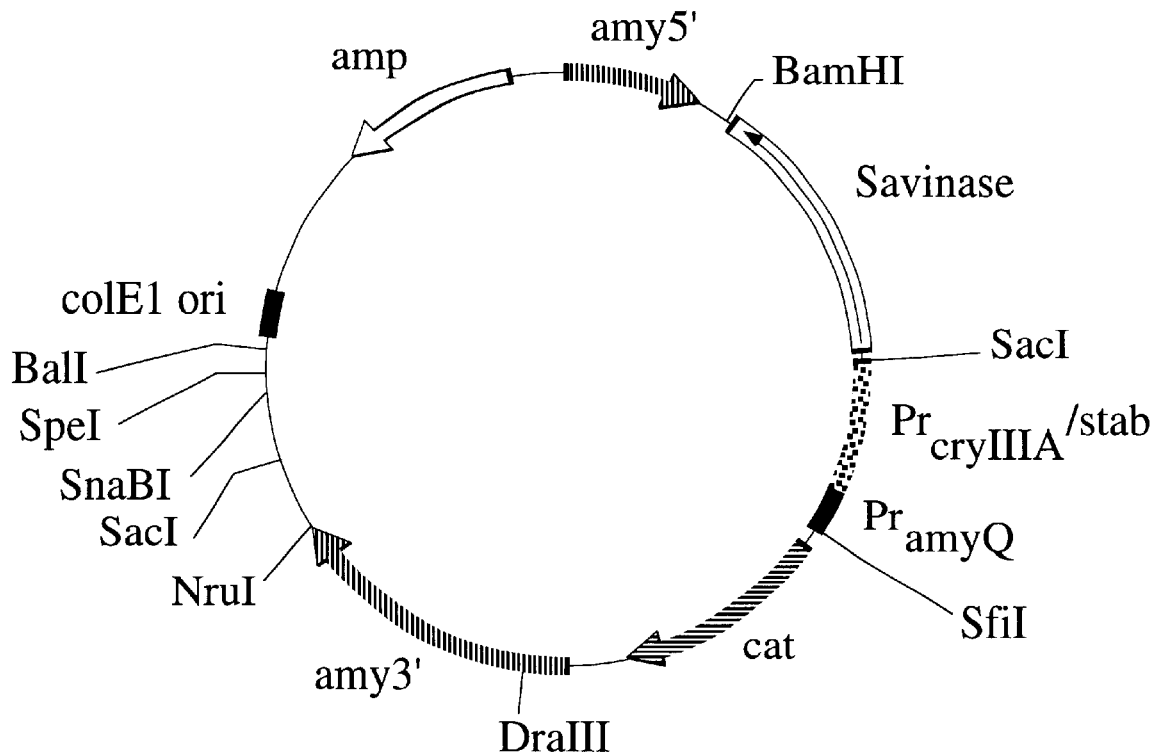
FIG. 18 shows a restriction map of pDG268MCS-Pr$_{amyQ}$/Pr$_{cryIIIA}$/cryIIIAstab/SAV.

Purified DNAs were ligated together and transformed in E. coli DH5α cells. Ampicillin resistant transformants were selected on LB plates supplemented with 100 μg of ampicillin per ml. A plasmid designated pDG268MCS-Pr$_{amyQ}$/Pr$_{cryIIIA}$/cryIIIAstab/SAV (FIG. 18) was isolated from one of the ampicillin resistant transformants. The plasmid structure was verified by digesting with SacI followed by gel-electrophoresis.

Example 16

Figure 19:
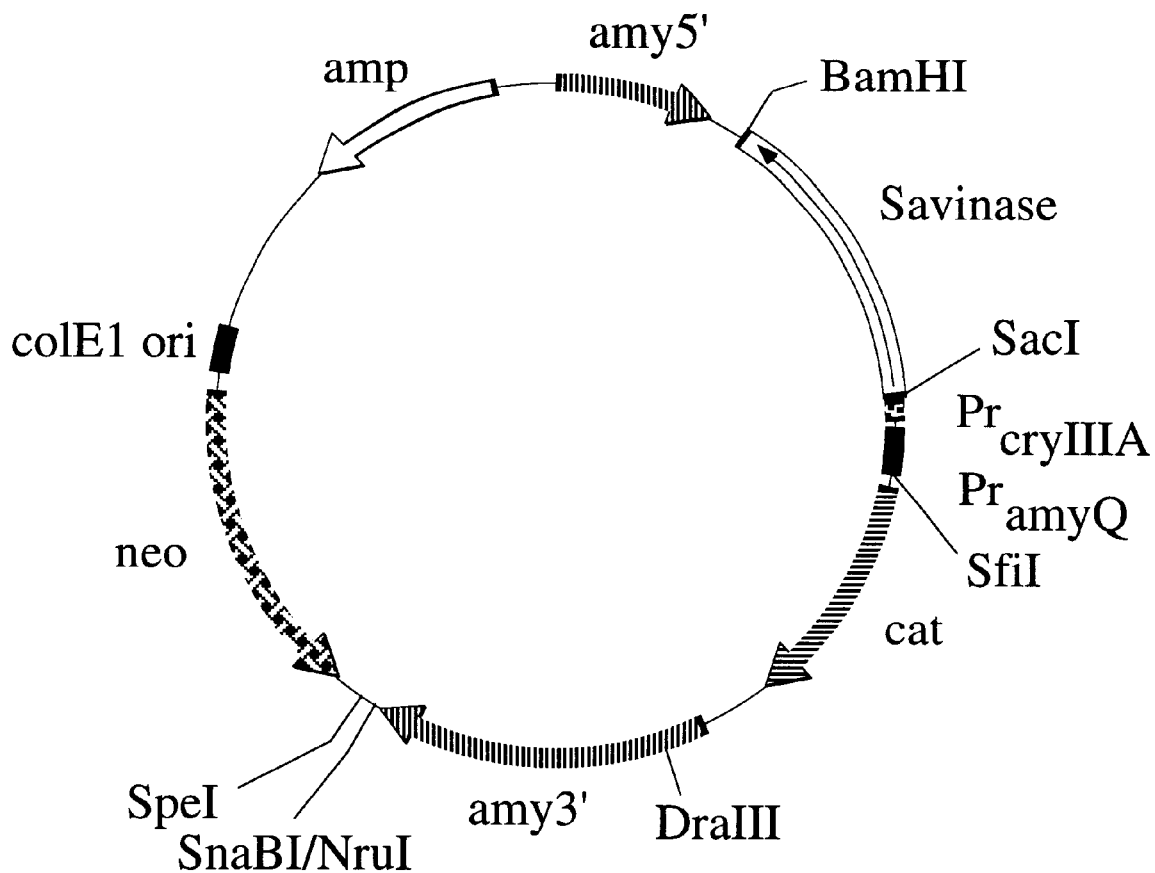
FIG. 19 shows a restriction map of pDG268MCSΔneo-Pr$_{amyQ}$/Pr$_{cryIIIA}$/SAV.

Construction of a Tandem amyQ-cryIIIA Promoter-SAVINAASE™ Gene Expression Cassette pDG268MCSΔneo-Pr$_{cryIIIA}$/SAV of Example 10 was digested with PacI and DraIII, and the approximately 6450 bp vector fragment was isolated by gel electrophoresis, as described in Example 1. The approximately 1790 bp PacI-DraIII fragment of pDG268MCS-Pr$_{amyQ}$/Pr$_{cryIIIA}$/cryIIIAstab/SAV (Example 15) bearing Pr$_{amyQ}$ and Pr$_{cryIIIA}$ was isolated by gel electrophoresis, as described in Example 1, and ligated with the vector fragment. E. coli DH5α was transformed with this ligation mixture and ampicillin resistant transformants were selected on LB plates supplemented with 100μg of ampicillin per ml. A plasmid designated pDG268MCSΔneo-Pr$_{amyQ}$/Pr$_{cryIIIA}$/SAV (FIG. 19) was purified from one of the ampicillin resistant transformants.

Example 17

Construction of a cryIIIA Stabilizer-SAVINASET Gene Expression Cassette pDG268MCSΔneo-cryIIIAstab/SAV was constructed as follows: pDG268MCSΔneo-Pr$_{cryIIIA}$/cryIIIAstab/SAV of Example 3 was digested with SfiI and treated with T4 DNA polymerase to remove the 3' overhangs. The plasmid was then digested with Asp718. The digest was subjected to agarose gel electrophoresis and the Asp718/blunted SfiI vector fragment of approximately 7540 bp was excised from the gel and the DNA extracted as described in Example 1.

pDG268MCSΔneo-Pr$_{cryIIIA}$/cryIIIAstab/SAV was digested with HindIII and treated with T4 DNA polymerase and dNTPs to fill in the recessed 3' ends. The plasmid was then digested with Asp718. The digest was separated by agarose gel electrophoresis and the fragment of approximately 920 bp containing the truncated cryIIIA promoter (only the "−10" region) and the downstream cryIIIA stabilizing sequence was excised from the gel and the DNA extracted as described in Example 1.

Figure 20:
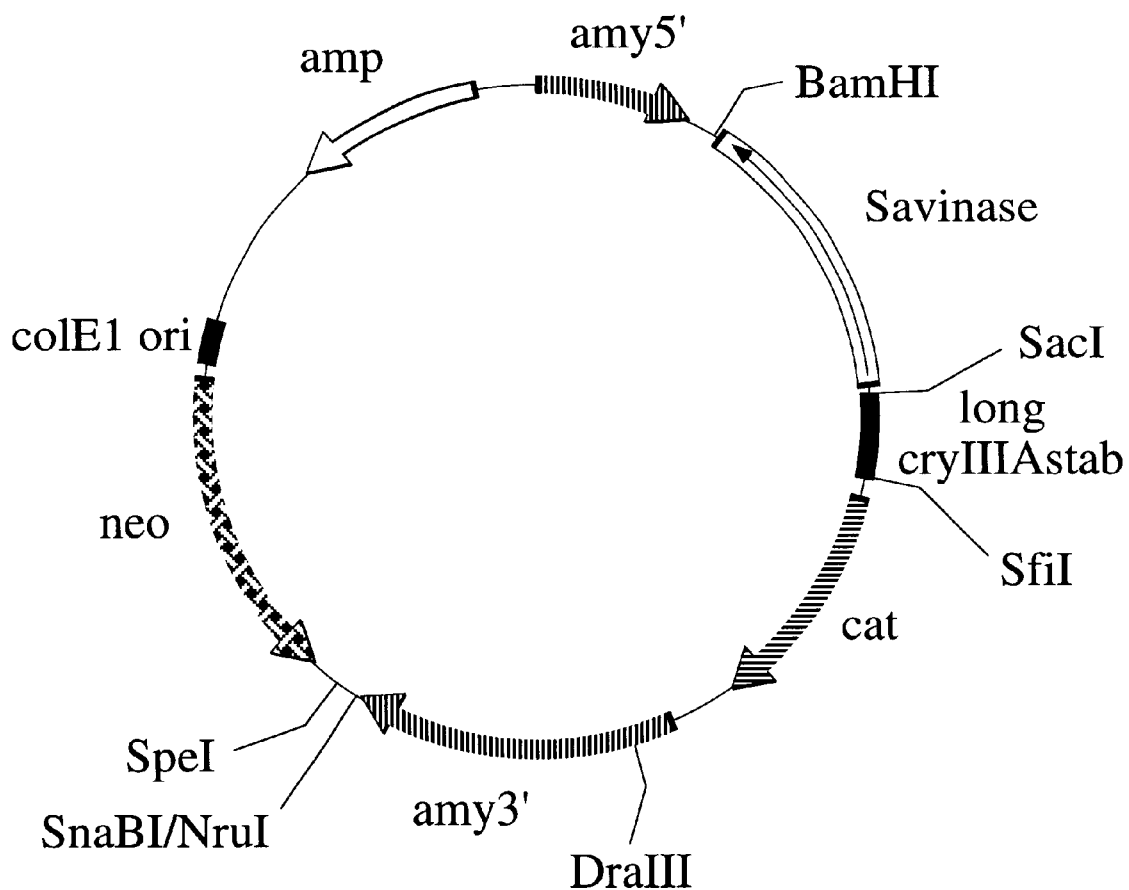
FIG. 20 shows a restriction map of pDG268MCSΔneo-long cryIIIAstab/SAV.

Purified DNAs were ligated together and the ligation mixture was transformed into E. coli DH5α cells. Ampicillin resistant transformants were selected on LB plates supplemented with 100 µg of ampicillin per ml. A plasmid designated pDG268MCSΔneo-cryIIIAstab/SAV (FIG. 20) was purified from one of the transformants.

Example 18

Construction of a "Consensus" amyQ Promoter

The following two oligonucleotides were annealed together and extended with Klenow fragment to generate a 68 bp double stranded fragment containing mutations (*) in the −10 and −35 regions of the amyQ promoter (highlighted in bold letters):

```
            SOE       **                      *
5'-GGAATAAAGGGGGGTTGACATTATTTTACTGATATGTATAATAT-3'    (SEQ ID NO. 19)

SacI
3'-AATAAAATGACTATACATATTATATTAAACATATTCTTTTACCTCGAG-5' (SEQ ID NO. 20)
```

A second double-stranded fragment comprising 137 bp of the upstream region of the amyQ promoter was generated by PCR using the following to primers:

```
      SfiI
5'-GGCCTTAAGGGCCTGCA-3'          (SEQ ID NO. 22)

SOE
5'-TGTCAACCCCCCTTTATTCCTT-3'     (SEQ ID NO. 23)
```

Both double-stranded DNA fragments were then fused together by traditional SOE methods (SOE overlaps are underlined and labeled) to generate a mutated version of the amyQ promoter designated "consensus" amyQ. The primers used in the SOE reaction to obtain the full-length fragment were 5'-GGCCTTAAGGGCCTGCA-3' (SEQ ID NO. 22) and 5'-GAGCTCCATTTTCTTATACAAATTATAT-3' (SEQ ID NO. 24).

The SOE reaction (50 µl) consisted of the following components: 50 ng of the 68 bp SOE fragment and 50 ng of the 137 bp SOE fragment, 1×Taq polymerase buffer, 200 µM each of dATP, dTTP, dGTP, and dCTP, and 2.5 units of Taq DNA polymerase. The conditions were one cycle at 95° C. for 3 minutes; 30 cycles each at 95° C. for 1 minute, 55° C. for 1 minute, and 72° C. for 1.5 minutes; after the third cycle 50 pmole of each of the two primers described above were added during the remaining 27 cycles to amplify the 185 bp promoter fragment. A final cycle was performed at 72° C. for 5 minutes.

The approximately 185 bp PCR product was subcloned directly into the pCRII vector according to the manufacturer's instructions and verified by DNA sequencing as described in Example 4 yielding pCRII-Pr$_{\text{"consensus" amyQ}}$ using forward and reverse M13 sequencing primers.

The sequence of the entire amyQ promoter including flanking restriction sites is shown in FIG. 21 (SEQ ID NO. 25). The following mutations were introduced into the nucleic acid sequence containing the wild-type amyQ promoter (SEQ ID NO. 25) to generate the "consensus" amyQ promoter (SEQ ID NO. 26): T to A and T to C in the −35 region (with respect to the transcription start site) at positions 135 and 136, respectively, and an A to T change in the −10 region at position 156 of SEQ ID NO. 25. Also a T to A change was inadvertently made at position 116 approximately 20 base pairs upstream of the −35 region as shown in FIG. 21 (SEQ ID NO. 27). This change apparently had no detrimental effect on promoter function since it is well removed from the critical −10 and −35 regions.

Example 19

Construction of a Short "Consensus" amyQ Promoter-SAVINASE™ Gene Expression Cassette The short "consensus" amyQ promoter was PCR amplified from pCRII-Pr$_{\text{"consensus" amyQ}}$ (Example 18) using the following oligonucleotide primers:

5'-GGCCTTAAGGGCCTGCTGTCCAGACTGTCCGCT-3' (SEQ ID NO. 28)

5'-GAGCTCCATTTTCTTATACAAATTATAT-3' (SEQ ID NO. 24)

The amplification reaction (100 µl) consisted of the following components: 50 ng of pCRII-Pr$_{\text{"consensus" amyQ}}$, 50 pmole of each primer, 1×Taq polymerase buffer, 200 µM each of dATP, dTTP, dGTP, and dCTP, and 1.0 unit of Taq polymerase. The amplification conditions were one cycle at 95° C. for 3 minutes; 30 cycles each at 95° C. for 1 minute, 50° C. for 1 minute, and 72° C. for 1.5 minutes; and a final cycle at 72° C. for 5 minutes.

The approximately 100 bp PCR product was cloned in the pCRII vector according to the manufacturer's instructions, yielding plasmid pCRII-Pr$_{\text{short "consensus" amyQ}}$, which was verified by DNA sequencing as described in Example 4, using forward and reverse M13 sequencing primers.

PCRII-Pr$_{\text{short "consensus" amyQ}}$ was digested with SfiI and SacI, and the approximately 100 bp fragment bearing the promoter was isolated by gel electrophoresis, as described in Example 1. pHP13amp-SAV of Example 5 was digested with SfiI and SacI, and the approximately 6430 bp vector fragment was isolated by gel electrophoresis, as described in Example 1. The purified were ligated together, Bacillus subtilis PL1801 spoIIE::Tn917 was transformed with this ligation mixture, and chloramphenicol resistant transformants were selected on TBAB plates supplemented with 5 µg of chloramphenicol per ml. A plasmid designated pHP13amp-Pr$_{\text{short "consensus" amyQ}}$/SAV was purified from one of the chloramphenicol resistant transformants.

Figure 22:
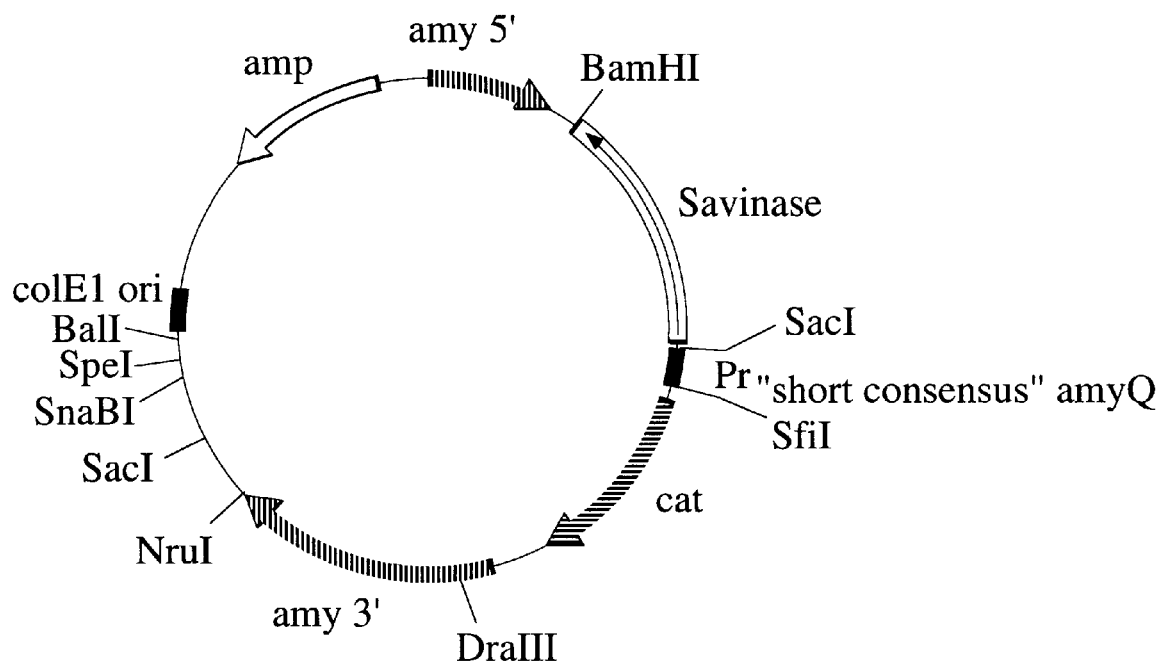
FIG. 22 shows a restriction map of pDG268MCS-Pr$_{short, "consensus" amyQ}$/SAV.

PHP1$^3$amp-Pr$_{\text{short "consensus" amyQ}}$/SAV was digested with SfiI and BamHI, and the approximately 1330 bp fragment bearing the Pr$_{\text{short "consensus" amyQ}}$/SAV cassette was isolated by gel electrophoresis, as described in Example 1. pDG268MCS of Example 1 was digested with SfiI and BamHI, and the approximately 6040 bp vector fragment was isolated by gel electrophoresis, as described in Example 1. The purified fragments were ligated together, E. coli DH5α was transformed with the ligation, and ampicillin resistant transformants were selected on LB plates supplemented with 100 µg of ampicillin per ml. A plasmid designated pDG268MCS-Pr$_{short\ "consensus"\ amyQ}$/SAV (FIG. 22) was purified from one of the ampicillin-resistant transformants and verified by digestion with SfiI and BamHI followed by gel electrophoresis.

Example 20

Figure 23:
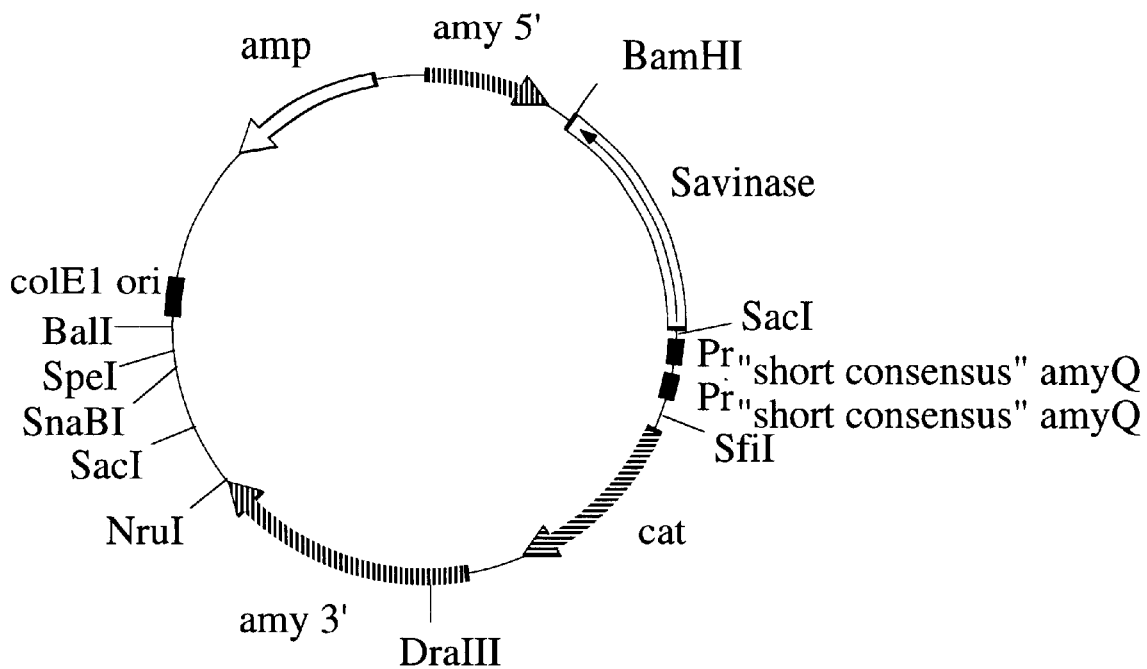
FIG. 23 shows a restriction map of pDG268MCS-Pr$_{short "consensus" amyQ dimer}$/SAV.

Construction of an Short "Consensus" amyQ Dimer Promoter-SAVINAASE™ Gene Expression Cassette pDG268MCS-Pr$_{short\ "consensus"\ amyQ}$/SAV of Example 19 was digested with SfiI, treated with T4 DNA polymerase to generate blunt ends, and digested with DraIII. The approximately 5830 bp vector fragment was isolated by gel electrophoresis, as described in Example 1. pDG268MCS-Pr$_{short\ "consensus"\ amyQ}$/SAV was also digested with Ecl136II and DraIII, and the approximately 1640 bp fragment bearing the Pr$_{short\ "consensus"\ amyQ}$/SAV was isolated by gel electrophoresis, as described in Example 1. The purified fragments were ligated together and transformed into E. coli DH5α cells. Ampicillin resistant transformants were selected on LB plates supplemented with 100 µg of ampicillin per ml. A plasmid designated pDG268MCS-Pr$_{short\ "consensus"\ amyQ\ dimer}$/SAV (FIG. 23) was purified from one of the ampicillin-resistant transformants and verified by DNA sequencing as described in Example 4 using construct-specific primers.

Example 21

Figure 24:
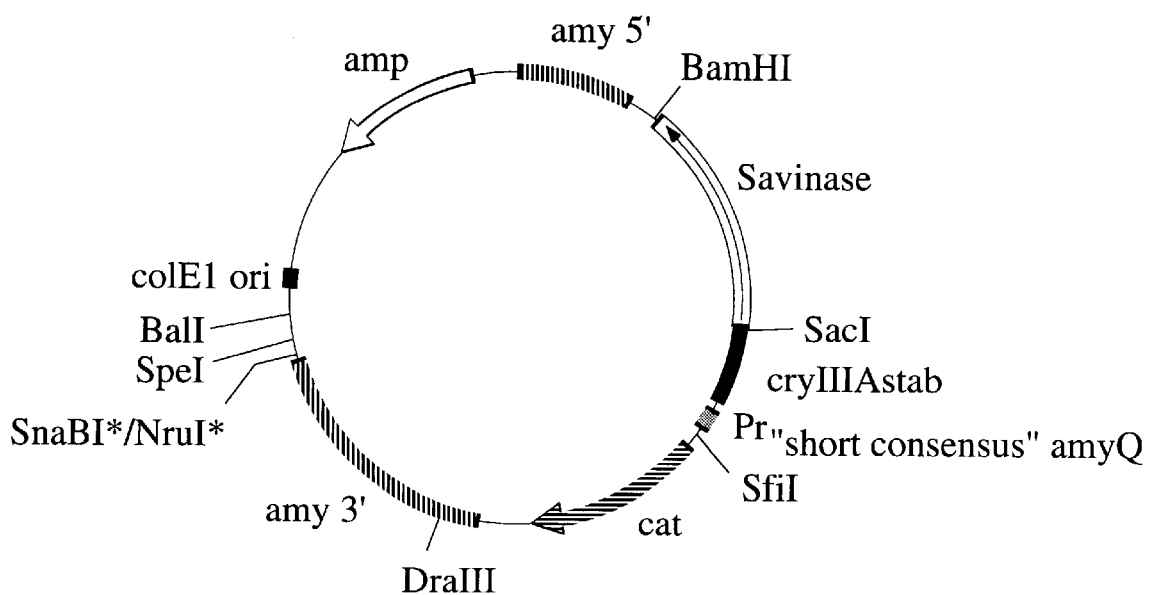
FIG. 24 shows a restriction map of pDG268MCSΔ-Pr$_{short "consensus" amyQ}$/cryIIIAstab/SAV.

Construction of a Short "Consensus" amyQ Promoter-cryIIIA Stabilizer-SAVINAASE™ Gene Expression Cassette pDG268MCAΔ-Pr$_{cryIIIA}$/cryIIIAstab/SAV of Example 2 was digested with SfiI and BamHI, and the approximately 5390 bp vector fragment was isolated by gel electrophoresis, as described in Example 1. pHP13amp-Pr$_{short\ "consensus"\ amyQ}$/SAV was digested with SfiI and BamHI, and the approximately 1330 bp fragment bearing the Pr$_{short\ "consensus"\ amyQ}$/SAV cassette was isolated by gel electrophoresis, as described in Example 1. The purified fragments were ligated together, E. coli DH5α was transformed with the ligation mixture, and ampicillin resistant transformants were selected on LB plates supplemented with 100 µg of ampicillin per ml. A plasmid designated pDG268MCAΔ-Pr$_{short\ "consensus"\ amyQ}$/SAV was purified from one of the ampicillin resistant transformants and verified by digestion with NcoI followed by gel electrophoresis.

pDG268MCAΔ-Pr$_{short\ "consensus"\ amyQ}$/SAV was digested with SacI and treated with calf intestine alkaline phosphatase to remove the 5' phosphate groups. pDG268MCS-Pr$_{amyL}$/cryIIIAstab/SAV of Example 11 was digested with SacI and the approximately 350 bp fragment bearing the cryIIIA stabilizer was isolated by gel electrophoresis, as described in Example 1. pDG268MCAΔ-Pr$_{short\ "consensus"\ amyQ}$/SAV and the stabilizer fragment were ligated, E. coli DH5α was transformed with the ligation mixture, and ampicillin resistant transformants were selected on LB plates supplemented with 100 µg of ampicillin per ml. A plasmid designated pDG268MCAΔ-Pr$_{short\ "consensus"\ amyQ}$/cryIIIAstab/SAV (FIG. 24) was purified from one of the ampicillin resistant transformants and verified by DNA sequencing as described in Example 4 using construct-specific primers.

Example 22

Figure 25:
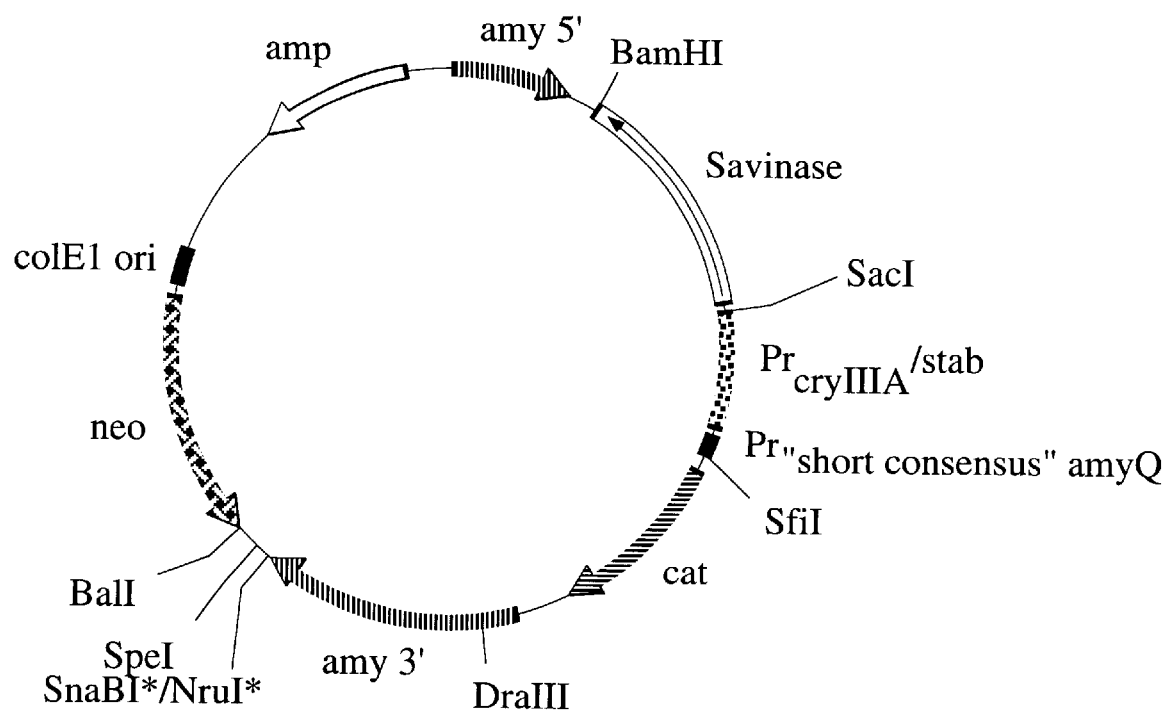
FIG. 25 shows a restriction map of pDG268MCSΔneo-Pr$_{short "consensus" amyQ}$/Pr$_{cryIIIA}$/cryIIIAstab/SAV.

Construction of a Tandem Short "Consensus" amyQ-cryIIIA Promoter-cryIIIA mRNA Stabilizer-SAVINAASE™ Gene Expression Cassette pDG268MCSΔneo-Pr$_{cryIIIA}$/cryIIIAstab/SAV of Example 3 was digested with SfiI and BamHI. The approximately 6780 bp vector fragment was isolated by gel electrophoresis, as described in Example 1. pDG268MCS-Pr$_{short\ "consensus"\ amyQ}$/SAV was digested with SfiI and BamHI. The approximately 1300 bp expression cassette fragment was isolated by gel electrophoresis, as described in Example 1. The purified fragments were ligated together and transformed into E. coli DH5α cells. Ampicillin resistant transformants were selected on LB plates supplemented with 100 µg of ampicillin per ml. A plasmid designated pDG268MCSΔneo-Pr$_{short\ "consensus"\ amyQ}$/SAV was purified from one of the ampicillin resistant transformants and verified by digestion with NcoI followed by gel electrophoresis.

pDG268MCSΔneo-Pr$_{cryIIIA}$/cryIIIAstab/SAV of Example 3 was digested with SfiI, treated with Klenow fragment to generate blunt ends, and digested with DraIII. The approximately 7060 bp vector fragment was isolated by gel electrophoresis, as described in Example 1. pDG268MCSΔneo-Pr$_{short\ "consensus"\ amyQ}$/SAV was digested with Ecl136II and DraIII, and the approximately 1540 bp fragment bearing the short "consensus" amyQ promoter was isolated by gel electrophoresis, as described in Example 1. The purified fragments were ligated together and transformed into E. coli DH5α cells. Ampicillin resistant transformants were selected on LB plates supplemented with 100 µg of ampicillin per ml. A plasmid designated pDG268MCSΔneo-Pr$_{short\ "consensus"\ amyQ}$/Pr$_{cryIIIA}$/cryIIIAstab/SAV (FIG. 25) was purified from one of the ampicillin resistant transformants and verified by digestion with NcoI followed by gel electrophoresis.

Example 23

Construction of a Short "Consensus" amyQ Trimer Promoter-SAVINASE™ Gene Expression Cassette pDG268MCS-Pr$_{short\ "consensus"\ amyQ\ dimer}$/SAV of Example 20 was digested with SfiI and BamHI, and the approximately 1230 bp fragment bearing the Pr$_{short\ "consensus"\ amyQ\ dimer}$/SAV cassette was isolated by gel electrophoresis, as described in Example 1. pDG268MCSΔneo-Pr$_{cryIIIA}$/cryIIIAstab/SAV of Example 3 was digested with SfiI and BamHI, and the approximately 6750 bp vector fragment was isolated by gel electrophoresis, as described in Example 1. The purified fragments were ligated together, E. coli DH5α was transformed with the ligation mixture, and ampicillin resistant transformants were selected on LB plates supplemented with 100 µg of ampicillin per ml. A plasmid designated pDG268MCSΔneo-Pr$_{short\ "consensus"\ amyQ\ dimer}$/SAV was purified from one of the ampicillin resistant transformants and verified by digestion with NcoI followed by gel electrophoresis.

pDG268MCSΔneo-Pr$_{short\ "consensus"\ amyQ}$/SAV of Example 23 was digested with Ecl136II and BamHI, and the approximately 6840 bp vector fragment was isolated by gel electrophoresis, as described in Example 1. pDG268MCSΔneo-Pr.*"short consensus amyQ" dimer*/SAV was digested with SfiI, treated with T4 DNA polymerase to generate blunt ends, and digested with BamHI. The approximately 1230 bp fragment bearing the Pr.*"short consensus amyQ" dimer*/SAV cassette was isolated by gel electrophoresis, as described in Example 1. The purified fragments were ligated together, *Bacillus subtilis* PL1801 spoIIE::Tn91 was transformed with the ligation, and chloramphenicol resistant transformants were selected on TBAB plates supplemented with 5 μg of chloramphenicol per ml. A chloramphenicol resistant, neomycin sensitive integrant containing the Pr$_{short}$ *"consensus" amyQ trimer*/SAV cassette was isolated.

Genomic DNA was isolated from this integrant using the QIAGEN bacterial DNA isolation protocol (QIAGEN, Inc., Santa Clarita, Calif., and a fragment bearing the short "consensus" amyQ trimer promoter was amplified from the genomic DNA by PCR using the following oligonucleotide primers:

5'-CCGTCGCTATTGTAACCAGT-3' (SEQ ID NO. 29)

5'-CGACTTCCTCTTCCTCAGAG-3' (SEQ ID NO. 30)

The amplification reaction (100 μl) consisted of the following components: 50 ng of genomic DNA, 50 pmole of each primer, 1×Taq polymerase buffer, 200 μM each of dATP, dTTP, dGTP, and dCTP, and 1.0 unit of Taq polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

The approximately 1078 bp PCR product was purified using the QIAquick PCR Purification Kit (QIAGEN Inc., Santa Clarita, Calif.), and the sequence of the short "consensus" amyQ trimer promoter was verified by DNA sequencing of the PCR product as described in Example 4 using construct-specific primers.

Example 24

Figure 26:
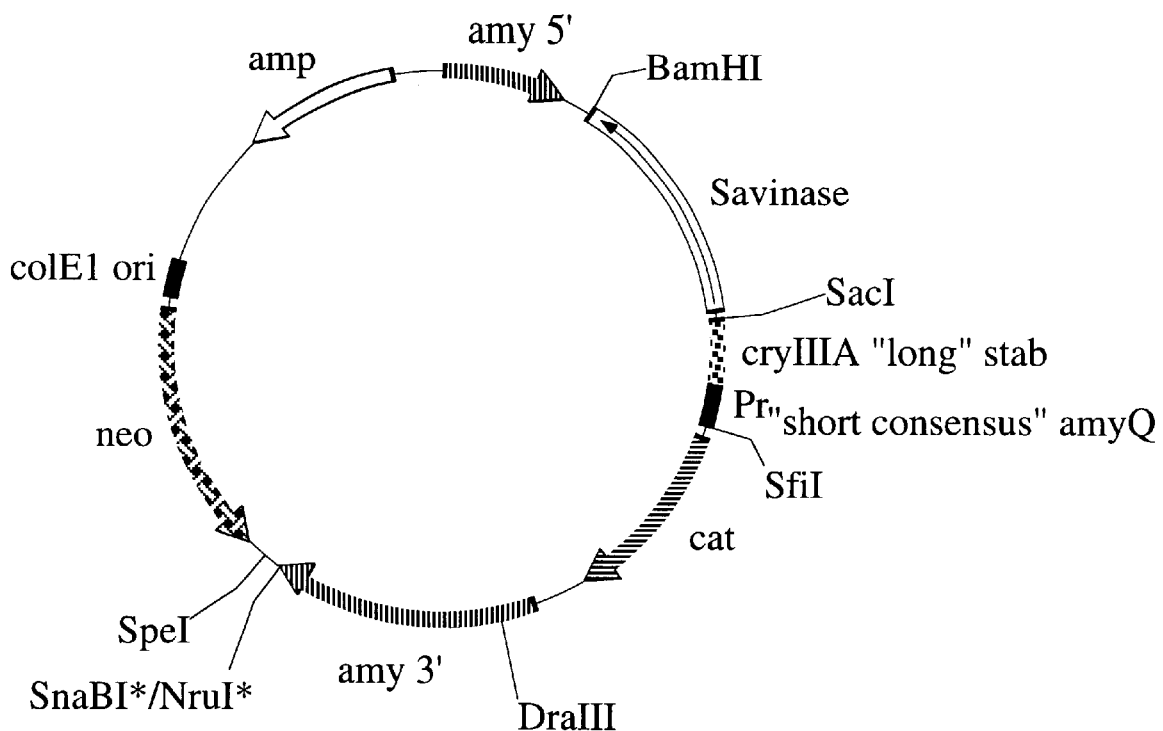
FIG. 26 shows a restriction map of pDG268MCSΔneo-Pr$_{short "consensus" amyQ}$/long cryIIIAstab/SAV.

Construction of a Short "Consensus" amyQ Promoter-long cryIIIA mRNA Stabilizer-SAVINAASE™ Gene Expression Cassette pDG268MCS-Pr$_{cryIIIA}$/cryIIIAstab/SAV of Example 9 was digested with HindIII, treated with T4 DNA polymerase and dNTPs to generate blunt ends, and digested with Asp718. The approximately 913 bp fragment bearing the long cryIIIA stabilizer and part of the SAVINAASE™ gene coding region was isolated by gel electrophoresis, as described in Example 1. pDG268MCSΔneo-Pr$_{short}$ *"consensus" amyQ*/SAV of Example 23 was digested with Ecl136II and Asp718, and the approximately 7700 bp vector fragment was isolated by gel electrophoresis, as described in Example 1. The purified fragments were ligated and transformed into *E. coli* DH5α cells. Ampicillin resistant transformants were selected on LB plates supplemented with 100 μg of ampicillin per ml. A plasmid designated pDG268MCSΔneo-Pr$_{short}$ *"consensus" amyQ*/long cryIIIAstab/SAV (FIG. 26) was purified from one of the ampicillin resistant transformants and verified by DNA sequencing as described in Example 4 using construct-specific primers.

Example 25

Construction of a "Short" amyQ Dimer Promoter-SAVINAASE™ Gene Expression Cassette The "short" amyQ promoter was PCR amplified from pCRII-Pr$_{amyQ}$ (Example 7) using the following oligonucleotide primers:

5'-GGCCTTAAGGGCCTGCTGTCCAGACTGTCCGCT-3' (SEQ ID NO. 31)

5'-GAGCTCCATTTTCTTATACAAATTATAT-3' (SEQ ID NO. 24)

The amplification reaction (100 μl) consisted of the following components: 50 ng of pCRII-Pr$_{amyQ}$, 50 pmole of each primer, 1×Taq polymerase buffer, 200 μM each of dATP, dTTP, dGTP, and dCTP, and 1.0 unit of Taq polymerase. The amplification conditions were one cycle at 95° C. for 3 minutes; 30 cycles each at 95° C. for 1 minute, 55° C. for 1 minute, and 72° C. for 1.5 minutes; and a final cycle at 72° C. for 5 minutes.

Figure 27:
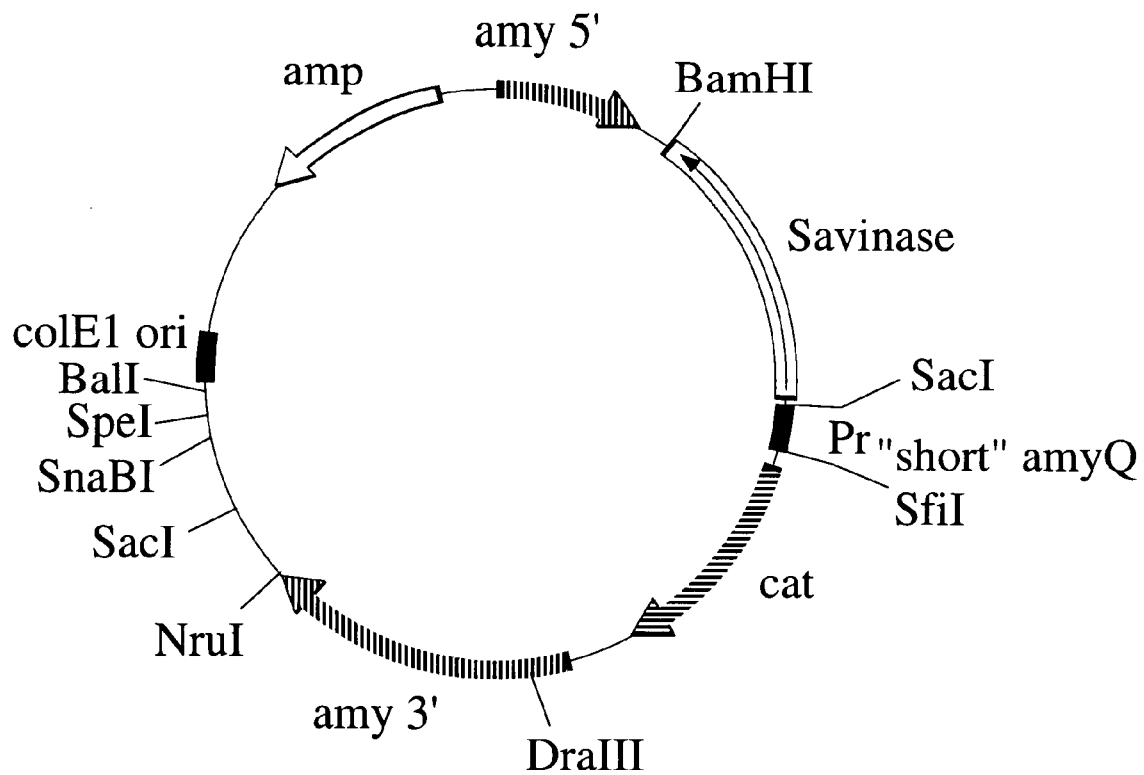
FIG. 27 shows a restriction map of pDG268MCS-Pr$_{"short" amyQ}$/SAV.
Figure 28:
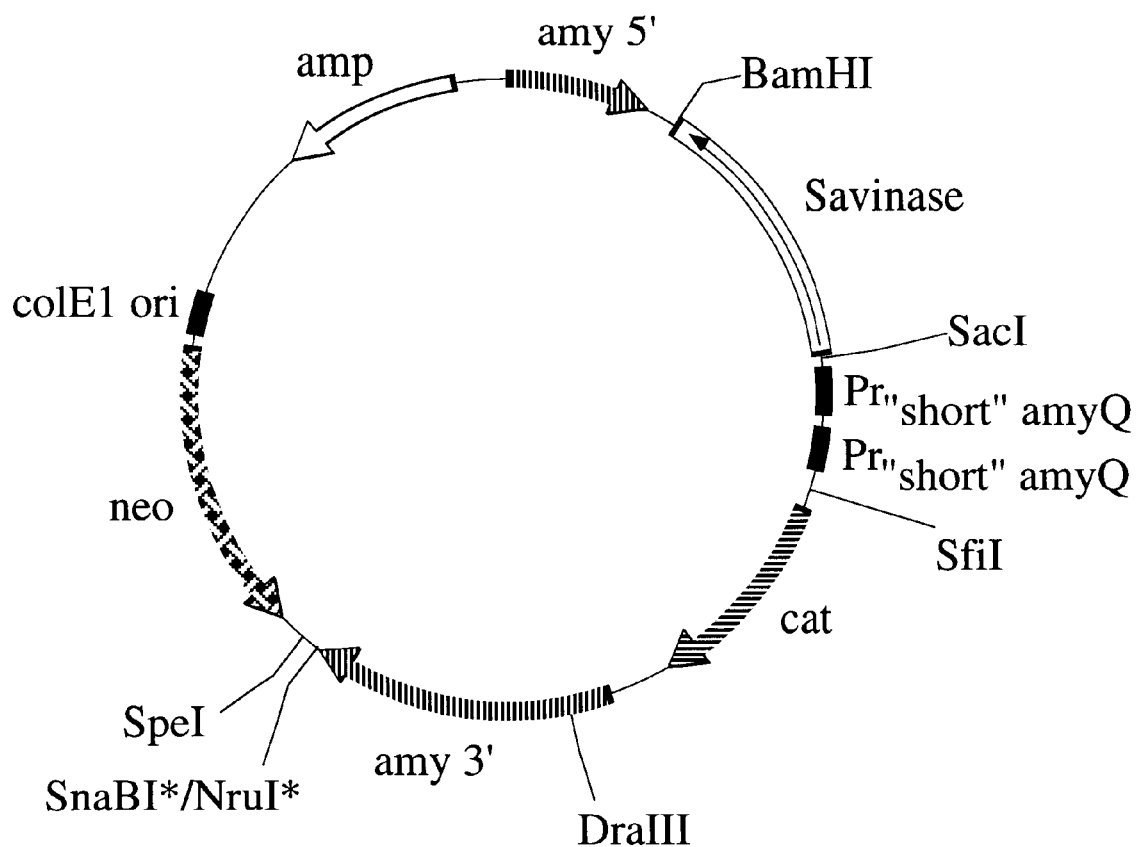
FIG. 28 shows a restriction map of pDG268Δneo-Pr$_{"short" amyQ dimer}$/SAV.

The approximately 100 bp PCR product was cloned in the pCRII vector according to the manufacturer's instructions, yielding plasmid pCRII-Pr.*"short" amyQ*, which was verified by DNA sequencing as described in Example 4, using forward and reverse M13 sequencing primers. Next, this plasmid was digested with SfiI and SacI and the approximately 100 bp promoter fragment was isolated by gel electrophoresis, as described in Example 1. pHP13amp-Pr$_{amyL}$/SAV from Example 6 was digested with SfiI and SacI and the approximately 6400 bp vector fragment was isolated by gel electrophoresis, as described in Example 1. These two fragments were then ligated together and transformed into *Bacillus subtilis* 168Δ4 cells (WO 98/22598). Chloramphenicol resistant transformants were selected on TBAB plates supplemented with 5 μg of chloramphenicol per ml and overlayed with 2% dried milk in TBAB agar in order to identify SAVINASE expressing clones by halo formation around transformant colonies. A plasmid designated pHP13amp- Pr.*"short" amyQ*/SAV was purified from one of the chloramphenicol resistant, halo-forming transformants and verified by digestion with PvuII followed by gel electrophoresis. Next, this plasmid was digested with SfiI and BamHI and the approximately 1300 bp expression cassette fragment was isolated by gel electrophoresis, as described in Example 1. pDG268MCS from Example 4 was digested with SfiI and BamHI. The two fragments were then ligated together and transformed into *E. coli* DH5α cells. Ampicillin resistant transformants were selected on LB plates supplemented with 100 μg of ampicilllin per ml. A plasmid designated pDG268MCS-Pr.*"short" amyQ*/SAV (FIG. 27) was purified from one of the ampicillin resistant transformants and verified by digestion with NcoI followed by gel electrophoresis.

pDG268MCS-Pr.*"short" amyQ*/SAV was digested with SfiI and BamHI, and the approximately 1330 bp fragment bearing the Pr.*"short" amyQ*/SAV expression cassette was isolated by gel electrophoresis, as described in Example 1. pDG268MCSΔneo-Pr$_{cryIIIA}$/cryIIIAstab/SAV of Example 3 was digested with SfiI and BamHI, and the approximately 6750 bp vector fragment was isolated by gel electrophoresis, as described in Example 1. The purified fragments were ligated together and transformed into *E. coli* DH5α cells. Ampicillin resistant transformants were selected on LB plates supplemented with 100 μg of ampicillin per ml. A plasmid designated pDG268Aneo-Pr.*"short" amyQ*/SAV was purified from one of the ampicillin resistant transformants and verified by digestion with NcoI followed by gel electrophoresis.

pDG268Aneo-Pr.*"short" amyQ*/SAV was digested with SfiI, treated with T4 DNA polymerase to generate blunt ends, and digested with DraIII. The approximately 6530 bp vector fragment was isolated by gel electrophoresis, as described in Example 1. pDG268Aneo-Pr.*"short" amyQ*/SAV was also digested with DraIII and Ecl136II, and the approximately 1640 bp fragment bearing the "short" amyQ promoter was isolated by gel electrophoresis, as described in Example 1. The purified fragments were ligated, E. coli DH5α was transformed with the ligation mixture, and ampicillin resistant transformants were selected on LB plates supplemented with 100 μg of ampicillin per ml. A plasmid designated pDG268Δneo-Pr$_{"short" \, amyQ \, dimer}$/SAV (FIG. 28) was purified from one of the ampicillin resistant transformants and verified by DNA sequencing as described in Example 4 using construct-specific primers.

Example 26

Figure 29:
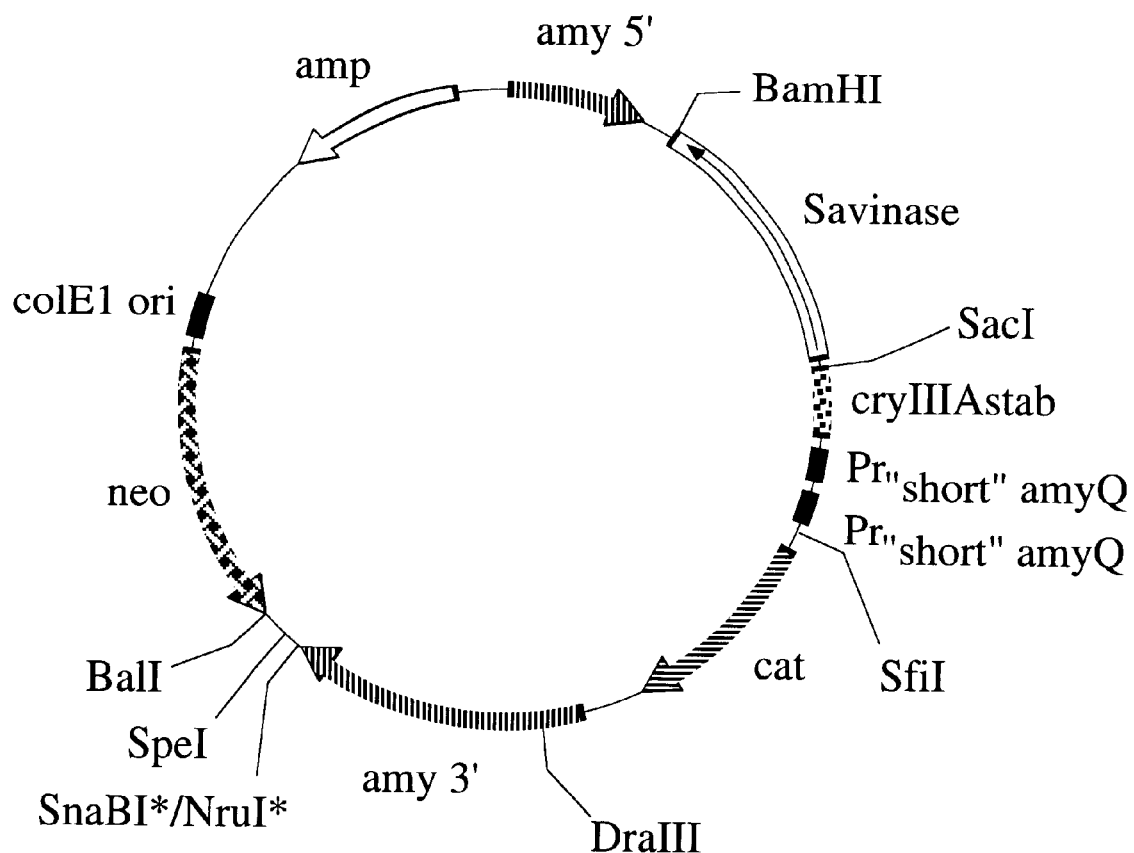
FIG. 29 shows a restriction map of pDG268Δneo-Pr$_{"short" amyQ dimer}$/cryIIIAstab/SAV.

Construction of a "Short" amyQ Dimer Promoter-cryIIIA mRNA Stabilizer-SAVINAASE™ Gene Expression Cassette pDG268Δneo-Pr$_{"short" \, amyQ \, dimer}$/SAV of Example 25 was digested with SacI and treated with calf intestine alkaline phosphatase to remove the 5' phosphate groups. pDG268MCS-Pr$_{amyL}$/cryIIIAstab/SAV of Example 11 was digested with SacI and the approximately 350 bp fragment bearing the cryIIIA stabilizer was isolated by gel electrophoresis, as described in Example 1. The cryIIIA stabilizer fragment was ligated to SacI-cut pDG268Δneo-Pr$_{"short" \, amyQ \, dimer}$/SAV. E. coli DH5α was transformed with the ligation mixture and ampicillin resistant transformants were selected on LB plates supplemented with 100 μg of ampicillin per ml. A plasmid designated pDG268Δneo-Pr$_{"short" \, amnyQ \, dimer}$/cryIIIAstab/SAV (FIG. 29) was purified from one of the ampicillin resistant transformants and verified by DNA sequencing as described in Example 4 using construct-specific primers.

Example 27

Copy Number of SAVINAASE™ Gene Expression Cassettes in Bacillus subtilis PL1801 spoIIE::Tn917 Integrants The SAVINAASE™ gene expression cassettes were each integrated into the amyE locus of Bacillus subtilis strain PL1801 spoIIE: :Tn917. Specifically, pDG268MCS derivatives containing the expression cassettes were digested with ScaI to linearize the plasmids. One microgram of linearized plasmid DNA was used to transform competent Bacillus subtilis PL1801 spoIIE::Tn917 to chloramphenicol resistance.

All transformants should contain a single copy of the expression cassette in the amyE locus as a result of a double cross-over event. This was confirmed by DNA dot blot analyses on chromosomal DNA to show the absence of the ampicillin-resistance gene (in integrants derived from pDG268MCS-or pDG268MCAΔ-based plasmids) or by neomycin sensitivity (in integrants derived from pDG268MCSΔneo-based plasmids).

Genomic DNA was isolated from Bacillus subtilis integrants using the QIAGEN bacterial DNA isolation protocol. For dot blot analysis, approximately 3μg of genomic DNA were denatured with 400 mM NaOH-10 mM EDTA in a total volume of 10 μL, incubating at room temperature for 10 minutes. One μl of denatured DNA was spotted on a Boehringer-Mannheim positively-charged nylon membrane (Boehringer-Mannheim Corporation, Indianapolis, Ind.) and fixed by UV-crosslinking with a UV STRATALINKER™ 2400 (Stratagene Cloning Systems, La Jolla, Calif.). The membrane was probed with a DNA probe specific to the ampicillin-resistance gene bla, using the GENIUS™ System, Version 2.0 (Boehringer-Mannheim Corporation, Indianapolis, Ind.). The blot was developed according to the GENIUS protocol using ATTOPHOS® detection reagent (Amersham International, Little Chalfont, UK). The probe was detected using the STORM™ 860 optical scanner and ImageQuant software (Molecular Dynamics, Sunnyvale, Calif.). Inability of the probe to bind to genomic DNA indicated absence of the bla gene, confrrming insertion of the plasmid by double cross-over.

The bla probe was created by labeling a PCR fragment with digoxigenin-11-dUTP using the Boehringer-Mannheim PCR DIG Probe Synthesis Kit (Boehringer-Mannheim Corporation, Indianapolis, Ind.). The PCR was performed using Amplitaq® Gold DNA polymerase and a Robocycler™ 40 thermal cycler (Stratagene Cloning Systems, La Jolla, Calif.) with the following temperature profile: 9 minutes at 95° C.; 30 cycles of 1 minute each at 95° C., 55° C., and 72° C.; and 3 minutes at 72° C. The probe was amplified from pUC118 using the following oligonucleotide primers:

```
5'-CTATGTGGCGCGGTATTATC-3'    (SEQ ID NO. 32)

5'-TTCATCCATAGTTGCCTGAC-3'    (SEQ ID NO. 33)
```

Once the transformants were confirmed to contain a single copy of the SAVINASE™ expression cassette, single-copy integrants for each expression cassette were analyzed by shake flask analysis.

Example 28

SAVINAASE™ Expression in Bacillus subtilis PL1801 spoIIE::Tn917

The single-copy integrants of each expression cassette described in Example 19 were grown to mid-log phase in 1 ml of LB broth at 37° C. Then 100 μl of each mid-log phase culture was inoculated into 50 ml of PS-1 medium composed of 10% sucrose, 4% soybean flour, 1% Na$_2$PO$_4$.12H$_2$O, 0.5% CaCO$_3$, and 0.01% pluronic acid. The cultures were shaken vigorously at 37° C. for 5 days. One ml aliquots were removed on days 3, 4, and 5, centrifuged at 12,000×g for 2 minutes, and 0.5 ml of each supernatant was frozen at −20° C. until all samples were taken. The frozen samples were then thawed and assayed for SAVINAASE™ activity using the following protocol to determine relative yields.

The assay for SAVINAASE™ activity was performed with casein fluorescein isothiocyanate as substrate. The casein fluorescein isothiocyanate stock solution was prepared according to Twining, 1984, *Analytical Biochemistry* 143: 30–34 and contained 0.5 mg of casein fluorescein isothiocyanate per 100 ml of 50 mM Tris-Cl pH 7.2 buffer. The assay reaction was initiated by the addition of 40 μl of the stock solution mixed 1:1 v/v with 0.25 M.borate pH 9.0 buffer to 10 μl of the enzyme sample diluted in 0.25 M borate pH 9.0 buffer as appropriate. The reaction was incubated for 10 minutes at 37° C. and then quenched by adding 150 μl of 5% trichloroacetic acid. The quenched reaction was placed in the cold room for 10 minutes and then centrifuged at top speed for 2 minutes. A 10 μl aliquot of the supernatant was transferred to a test tube containing 2 ml of 0.5 M borate pH 9.0 buffer and mixed well. A 200 tl aliquot of this solution was transferred to a black "U" bottom 96 well plate (Dynatech Laboratories, Inc., Chantilly, Va.) and the fluorescence was measured using a Fluorolite 1000 fluorimeter (Dynatech Laboratories, Inc., Chantilly, Va.) using channel 3 at reference setting 1176 and a lamp voltage at 4. 1V. SAVINASE™ activity was calculated by reference to a standard curve generated with a SAVINASE™ standard (Novo Nordisk A/S, Bagsværd, Denmark) in the range of 1.8–9.0 NPU (Novo Protease Unit) per ml. The activity of the standard is determined according to Novo Analytical Method AF 220/1-GB available upon request from Novo Nordisk A/S, Bagsværd, Denmark.

The results are shown in Table 1. The amyQ, amyL, and cryIIIA promoters (without the stabilizer sequence) were all about equal in strength based on the SAVINASE™ assay results. When the cryIIIA mRNA stabilizer sequence was placed downstream of these promoters their activities increased substantially (at least a 1.7-fold increase in expression levels). However, when the cryIIIA mRNA stabilizer sequence was included downstream of the tandem promoters, the activities were more than four-fold higher than the single promoters by themselves and more than 2-fold higher than the single promoters with the cryIIIA mRNA stabilizer sequence included. When the cryIIIA mRNA stabilizer sequence was used without a promoter, SAVINASE™ expression was very low, indicating that the enhancing effect of the stabilizer sequence was not due to promoter activity within the stabilizer sequence. Therefore, by placing a promoter such as the amyQ or amyL promoter upstream of the cryIIIA promoter and its mRNA stabilizing sequence, a tandem promoter can be created which is far superior activity to any single promoter by itself.

The results also indicated it was possible to obtain higher levels of gene expression by modifying a promoter such as the amyQ promoter as described herein to make it a stronger promoter, i.e., the "consensus" amyQ and "short consensus" amyQ promoters. Both of these promoters were approximately 4-fold stronger than the wild-type amyQ promoter from which they were derived. In addition, higher levels of expression could be obtained by placing the cryIIA long mRNA stabilizer sequence downstream of the "short consensus" promoter. This particular combination resulted in saturating levels of mRNA and maximum levels of SAVINAASE™ expression, levels comparable to a fully amplified strain (a 6-fold increase over the wild-type amyQ promoter alone).

In addition, the results showed that higher levels of expression could be obtained by assembling more than one copy of a single promoter in a "head-to-tail" fashion. This is clearly illustrated by comparing the levels of expression obtained from the single short "consensus" amyQ promoter, a dimer short "consensus" amyQ promoter, and a trimer short "consensus" amyQ promoter. SAVINAASE™ expression levels were 1.5-fold and 1.8-fold higher, respectively, for the latter two in comparison to the monomer promoter.

The overall results demonstrated the ability to increase transcription of a single-copy gene using the following approaches: The creation of tandem promoters by placing promoters such as amyQ and amyL upstream of the cryIIIA promoter and its mRNA stabilizing sequence, the creation of a "consensus" amyQ promoter with the cryIIIA mRNA stabilizing sequence, and the creation of tandem copies of a single promoter such as the short "consensus" amyQ dimer and trimer promoters. All of these approaches lead to significantly higher levels of gene expression when compared to the levels obtained using single promoters such as amyQ and amyL.

TABLE 1

| Expression cassette | Relative SAVINASE ™ activity |
|---|---|
| $Pr_{amyL}$/SAV | 90% |
| $Pr_{amyQ}$/SAV | 100% |
| $Pr_{short\ amyQ}$/SAV | 100% |
| $Pr_{cryIIIA}$/cryIIIAstab/SAV | 350% |
| $Pr_{cryIIIA}$/SAV | 100% |
| $Pr_{amyL}$/cryIIIAstab/SAV | 230% |
| $Pr_{amyQ}$/cryIIIAstab/SAV | 170% |
| $Pr_{amyL}$/$Pr_{cryIIIA}$/SAV | 90% |
| $Pr_{amyQ}$/$Pr_{cryIIIA}$/SAV | 80% |
| $Pr_{amyL}$/$Pr_{cryIIIA}$/cryIIIAstab/SAV | 570% |
| $Pr_{amyQ}$/$Pr_{cryIIIA}$/cryIIIAstab/SAV | 540% |
| $Pr_{\text{"short" amyQ cimer}}$/SAV | 210% |
| $Pr_{\text{"short" amyQ dimer}}$/cryIIIAstab/SAV | 310% |
| $Pr_{short\ \text{"consensus" amyQ}}$/SAV | 370% |
| $Pr_{short\ \text{"consensus" amyQ}}$/cryIIIAstab/SAV | 620% |
| $Pr_{short\ \text{"consensus" amyQ}}$/long cryIIIAstab/SAV | 550% |
| $Pr_{short\ \text{"consensus" amyQ}}$/$Pr_{cryIIIA}$/cryIIIAstab/SAV | 700% |
| $Pr_{short\ \text{"consensus" amyQ dimer}}$/SAV | 570% |
| $Pr_{short\ \text{"consensus" amyQ trimer}}$/SAV | 670% |
| Long cryIIIAstab/SAV | 3% |

What is claimed is:

1. A method for producing a polypeptide, comprising:
   (a) cultivating a Bacillus cell in a medium conducive for the production of the polypeptide, wherein the Bacillus cell comprises a nucleic acid construct comprising a tandem promoter in which each promoter sequence of the tandem promoter is operably linked to a nucleic acid sequence encoding the polypeptide, wherein the tandem promoter comprises promoters selected from the group consisting of the amyL promoter, amyQ promoter, aprH promoter, cryIIIA promoter, subtilisin Carlsberg gene promoter, and consensus promoters of the amyL promoter, amyQ promoter, aprH promoter, cryIIIA promoter, and subtilisin Carlsberg gene promoter having the sequence TTGACA for the "−35" region and TATAAT for the "−10" region; and
   (b) isolating the polypeptide from the cultivation medium.

2. The method of claim 1, wherein the tandem promoter comprises at least two copies of a promoter selected from the group consisting of the amyL promoter, amyQ promoter, aprH promoter, cryIIIA promoter, subtilisin Carlsberg gene promoter, and consensus promoters of the amyL promoter, amyQ promoter, aprH promoter, cryIIIA promoter, and subtilisin Carlsberg gene promoter having the sequence TTGACA for the "−35" region and TATAAT for the "−10" region.

3. The method of claim 1, wherein the tandem promoter comprises the amyL promoter and the cryIIIA promoter.

4. The method of claim 1, wherein the Bacillus cell contains one or more copies of the nucleic acid construct.

5. The method of claim 1, wherein the nucleic acid construct further comprises a selectable marker gene.

6. The method of claim 1, wherein the Bacillus cell contains no selectable marker gene.

7. The method of claim 1, wherein the nucleic acid sequence encodes a polypeptide heterologous to the Bacillus cell.

8. The method of claim 1, wherein the polypeptide is a hormone or variant thereof, enzyme, receptor or portion thereof, antibody or portion thereof, or reporter.

9. The method of claim 8, wherein the enzyme is an oxidoreductase, transferase, hydrolase, lyase, isomerase, or ligase.

10. The method of claim 1, wherein the Bacillus host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cell.

11. A method for producing a polypeptide, comprising:
   (a) cultivating a Bacillus cell in a medium conducive for the production of the polypeptide, wherein the Bacillus cell comprises a nucleic acid construct comprising (i) a consensus promoter obtained from *Bacillus amyloliquefaciens* alpha-amylase gene (amy Q) or *Bacillus subtilis* alpha-amylase gene (amy E) having the sequence TTGACA for the "−35" region and TATAAT for the "−10" region operably linked to a single copy of a nucleic acid sequence encoding the polypeptide and (ii) an mRNA processing/stabilizing sequence located downstream of the consensus promoter and upstream of the nucleic acid sequence encoding the polypeptide; and (b) isolating the polypeptide from the cultivation medium.

12. The method of claim 11, wherein the mRNA processing/stabilizing sequence is the cryIIIA mRNA processing/stabilizing sequence.

13. The method of claim 11, wherein the mRNA processing/stabilizing sequence is the SP82 mRNA processing/stabilizing sequence.

14. The method of claim 11, wherein the mRNA processing/stabilizing sequence generates mRNA transcripts essentially of the same size.

15. The method of claim 11, wherein the Bacillus cell contains one or more copies of the nucleic acid construct.

16. The method of claim 11, wherein the nucleic acid construct further comprises a selectable marker gene.

17. The method of claim 11, wherein the Bacillus cell contains no selectable marker gene.

18. The method of claim 11, wherein the nucleic acid sequence encodes a polypeptide heterologous to the Bacillus cell.

19. The method of claim 11, wherein the polypeptide is a hormone or variant thereof, enzyme, receptor or portion thereof, antibody or portion thereof, or reporter.

20. The method of claim 19, wherein the enzyme is an oxidoreductase, transferase, hydrolase, lyase, isomerase, or ligase.

21. The method of claim 19, wherein the enzyme is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

22. The method of claim 11, wherein the Bacillus host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cell.

23. The method of claim 11, wherein the Bacillus cell is a *Bacillus subtilis* cell.

* * * * *

SEQUENCE LISTING

<160> NUMBER OF SEQ ID NOS: 33

<210> SEQ ID NO: 1
<211> LENGTH: 54
<212> TYPE: DNA
<213> ORGANISM: Bacillus

<400> SEQUENCE: 1
aattggcctt aagggcccgg gacgtcaagc ttatcgatgc ggatccgcgg ccgc        54

<210> SEQ ID NO: 2
<211> LENGTH: 51
<212> TYPE: DNA

<210> SEQ ID NO: 2
<211> LENGTH: 51
<212> TYPE: DNA
<213> ORGANISM: Bacillus

<400> SEQUENCE: 2
ccggaattcc cgggccctgc agttcgaata gctacgccta ggcgccggcg c        51

<210> SEQ ID NO: 3
<211> LENGTH: 58
<212> TYPE: DNA
<213> ORGANISM: Bacillus

<400> SEQUENCE: 3
agctaggcct taagggcccg ggacgtcgag ctcaagcttg cggccgccat ggtcgacg    58

<210> SEQ ID NO: 4
<211> LENGTH: 58
<212> TYPE: DNA
<213> ORGANISM: Bacillus

<400> SEQUENCE: 4
tccggaattc ccgggccctg cagctcgagt tcgaacgccg gcggtaccag ctgcttaa    58

<210> SEQ ID NO: 5
<211> LENGTH: 37
<212> TYPE: DNA
<213> ORGANISM: Bacillus

<400> SEQUENCE: 5
ctccgggccc atctgagctc tataaaatg aggaggg                           37

<210> SEQ ID NO: 6
<211> LENGTH: 27
<212> TYPE: DNA
<213> ORGANISM: Bacillus

<400> SEQUENCE: 6
cctcggatcc atacacaaaa aaacgct                                     27

<210> SEQ ID NO: 7
<211> LENGTH: 37
<212> TYPE: DNA
<213> ORGANISM: Bacillus

<400> SEQUENCE: 7
ccaggcctta agggccgcat gcgtccttct ttgtgct                          37

<210> SEQ ID NO: 8
<211> LENGTH: 30
<212> TYPE: DNA
<213> ORGANISM: Bacillus

<400> SEQUENCE: 8
ccagagctcc tttcaatgtg taacatatga                                  30

<210> SEQ ID NO: 9
<211> LENGTH: 42
<212> TYPE: DNA
<213> ORGANISM: Bacillus

<400> SEQUENCE: 9
tttggcctta agggcctgca atcgattgtt tgagaaaaga ag                    42

<210> SEQ ID NO: 10
<211> LENGTH: 43

```
<212> TYPE: DNA
<213> ORGANISM: Bacillus

<400> SEQUENCE: 10
tttgagctcc attttcttat acaaattata ttttacatat cag            43

<210> SEQ ID NO: 11
<211> LENGTH: 30
<212> TYPE: DNA
<213> ORGANISM: Bacillus

<400> SEQUENCE: 11
gagacccggg agctttcagt gaagtacgtg                           30

<210> SEQ ID NO: 12
<211> LENGTH: 19
<212> TYPE: DNA
<213> ORGANISM: Bacillus

<400> SEQUENCE: 12
ggggcgttac aattcaaag                                       19

<210> SEQ ID NO: 13
<211> LENGTH: 27
<212> TYPE: DNA
<213> ORGANISM: Bacillus

<400> SEQUENCE: 13
gggccctcga acgtaagat gaaacct                               27

<210> SEQ ID NO: 14
<211> LENGTH: 29
<212> TYPE: DNA
<213> ORGANISM: Bacillus

<400> SEQUENCE: 14
gagctccata atacataatt ttcaaactg                            29

<210> SEQ ID NO: 15
<211> LENGTH: 21
<212> TYPE: DNA
<213> ORGANISM: Bacillus

<400> SEQUENCE: 15
cagccatcac attgtgaaat c                                    21

<210> SEQ ID NO: 16
<211> LENGTH: 23
<212> TYPE: DNA
<213> ORGANISM: Bacillus

<400> SEQUENCE: 16
gagctctatc tttaattaag ctt                                  23

<210> SEQ ID NO: 17
<211> LENGTH: 23
<212> TYPE: DNA
<213> ORGANISM: Bacillus

<400> SEQUENCE: 17
gagctcgaac ttgttcatgt gaa                                  23

<210> SEQ ID NO: 18
```

```
<211> LENGTH: 23
<212> TYPE: DNA
<213> ORGANISM: Bacillus

<400> SEQUENCE: 18
gagctcataa tacataattt tca                                              23

<210> SEQ ID NO: 19
<211> LENGTH: 44
<212> TYPE: DNA
<213> ORGANISM: Bacillus

<400> SEQUENCE: 19
ggaataaagg ggggttgaca ttattttact gatatgtata atat                       44

<210> SEQ ID NO: 20
<211> LENGTH: 48
<212> TYPE: DNA
<213> ORGANISM: Bacillus

<400> SEQUENCE: 20
aataaaatga ctatacatat tatattaaac atattctttt acctcgag                   48

<210> SEQ ID NO: 21
<211> LENGTH: 3050
<212> TYPE: DNA
<213> ORGANISM: a:Bacillus

<400> SEQUENCE: 21
tcgaaacgta agatgaaacc ttagataaaa gtgctttttt tgttgcaatt gaagaattat      60
taatgttaag cttaattaaa gataatatct ttgaattgta acgcccctca aaagtaagaa     120
ctacaaaaaa agaatacgtt atatagaaat atgtttgaac cttcttcaga ttacaaatat     180
attcggacgg actctacctc aaatgcttat ctaactatag aatgacatac aagcacaacc     240
ttgaaaattt gaaaatataa ctaccaatga acttgttcat gtgaattatc gctgtattta     300
attttctcaa ttcaatatat aatatgccaa tacattgtta caagtagaaa ttaagacacc     360
cttgatagcc ttactatacc taacatgatg tagtattaaa tgaatatgta aatatattta     420
tgataagaag cgacttattt ataatcatta catattttc tattggaatg attaagattc      480
caatagaata gtgtataaat tatttatctt gaaggaggg atgcctaaaa acgaagaaca      540
ttaaaaacat atatttgcac cgtctaatgg atttatgaaa aatcattta tcagtttgaa      600 aattatgtat tatgataaga aagggaggaa gaaaaatgaa tccgaacaat cgaagtgaac     660
atgatacaat aaaaactact gaaaataatg aggtgccaac taccatgtt caatatcctt      720 tagcggaaac tccaaatcca acactagaag atttaaatta taagagtttt ttaagaatga     780
ctgcagataa taatacggaa gcactagata gctctacaac aaaagatgtc attcaaaaag     840
gcatttccgt agtaggtgat ctcctaggcg tagtaggttt cccgtttggt ggagcgcttg     900 tttcgttta tacaaacttt ttaaatacta tttggccaag tgaagacccg tggaaggctt      960
ttatggaaca agtagaagca ttgatggatc agaaaatagc tgattatgca aaaaataaag    1020
ctcttgcaga gttacaggc cttcaaaata atgtcgaaga ttatgtgagt gcattgagtt     1080
catggcaaaa aaatcctgtg agttcacgaa atccacatag ccaggggcgg ataagagagc    1140
tgttttctca agcagaaagt cattttcgta ttcaatgcc ttcgtttgca atttctggat     1200
acgaggttct atttctaaca acatatgcac aagctgccaa cacacattta tttttactaa    1260
aagacgctca aatttatgga gaagaatggg gatacgaaaa agaagatatt gctgaatttt    1320
```

```
ataaaagaca actaaaactt acgcaagaat atactgacca ttgtgtcaaa tggtataatg    1380
ttggattaga taaattaaga ggttcatctt atgaatcttg ggtaaacttt aaccgttatc    1440
gcagagagat gacattaaca gtattagatt taattgcact atttccattg tatgatgttc    1500
ggctataccc aaaagaagtt aaaaccgaat taacaagaga cgttttaaca gatccaattg    1560
tcggagtcaa caaccttagg ggctatggaa caaccttctc taatatagaa aattatattc    1620
gaaaaccaca tctatttgac tatctgcata gaattcaatt tcacacgcgg ttccaaccag    1680
gatattatgg aaatgactct ttcaattatt ggtccggtaa ttatgtttca actagaccaa    1740
gcataggatc aaatgatata atcacatctc cattctatgg aaataaatcc agtgaacctg    1800
tacaaaattt agaatttaat ggagaaaaag tctatagagc cgtagcaaat acaaatcttg    1860
cggtctggcc gtccgctgta tattcaggtg ttacaaaagt ggaatttagc caatataatg    1920
atcaaacaga tgaagcaagt acacaaacgt acgactcaaa aagaaatgtt ggcgcggtca    1980
gctgggattc tatcgatcaa ttgcctccag aaacaacaga tgaacctcta gaaaagggat    2040
atagccatca actcaattat gtaatgtgct ttttaatgca gggtagtaga ggaacaatcc    2100
cagtgttaac ttggacacat aaaagtgtag acttttttaa catgattgat tcgaaaaaaa    2160
ttacacaact tccgttagta aaggcatata agttacaatc tggtgcttcc gttgtcgcag    2220
gtcctaggtt tacaggagga gatatcattc aatgcacaga aaatggaagt gcggcaacta    2280
tttacgttac accggatgtg tcgtactctc aaaaatatcg agctagaatt cattatgctt    2340
ctacatctca gataacattt acactcagtt tagacggggc accatttaat caatactatt    2400
tcgataaaac gataaataaa ggagacacat taacgtataa ttcatttaat ttagcaagtt    2460
tcagcacacc attcgaatta tcagggaata acttacaaat aggcgtcaca ggattaagtg    2520
ctggagataa agtttatata gacaaaattg aatttattcc agtgaattaa attaactaga    2580
aagtaaagaa gtagtgacca tctatgatag taagcaaagg ataaaaaaat gagttcataa    2640
aatgaataac atagtgttct tcaactttcg ctttttgaag gtagatgaag aacactattt    2700
ttattttcaa aatgaaggaa gttttaaata tgtaatcatt taaagggaac aatgaaagta    2760
ggaaataagt cattatctat aacaaaataa cattttatata tagccagaaa tgaattataa    2820
tattaatctt ttctaaattg acgttttcct aaacgttcta tagcttcaag acgcttagaa    2880
tcatcaatat ttgtatacag agctgttgtt tccatcgagt tatgtcccat ttgattcgct    2940
aatagaacaa gatctttatt ttcgttataa tgattggttg cataagtatg gcgtaattta    3000
tgagggcttt tcttttcatc aaaagccctc gtgtatttct ctgtaagctt               3050
```

<210> SEQ ID NO: 22
<211> LENGTH: 17
<212> TYPE: DNA
<213> ORGANISM: Bacillus

<400> SEQUENCE: 22

```
ggccttaagg gcctgca                                                     17
```

<210> SEQ ID NO: 23
<211> LENGTH: 22
<212> TYPE: DNA
<213> ORGANISM: Bacillus

<400> SEQUENCE: 23

```
tgtcaacccc cctttattcc tt                                               22
```

<210> SEQ ID NO: 24
<211> LENGTH: 28
<212> TYPE: DNA
<213> ORGANISM: Bacillus

<400> SEQUENCE: 24
gagctccatt ttcttataca aattatat                                28

<210> SEQ ID NO: 25
<211> LENGTH: 185
<212> TYPE: DNA
<213> ORGANISM: Bacillus

<400> SEQUENCE: 25
ggccttaagg gcctgcaatc gattgtttga gaaaagaaga agaccataaa aataccttgt    60
ctgtcatcag acagggtatt ttttatgctg tccagactgt ccgctgtgta aaaatagga   120 ataaggggg gttgttatta ttttactgat atgtaaaata taatttgtat aagaaaatgg   180
agctc                                                              185

<210> SEQ ID NO: 26
<211> LENGTH: 185
<212> TYPE: DNA
<213> ORGANISM: Bacillus

<400> SEQUENCE: 26
ggccttaagg gcctgcaatc gattgtttga gaaaagaaga agaccataaa aataccttgt    60
ctgtcatcag acagggtatt ttttatgctg tccagactgt ccgctgtgta aaaaaagga   120 ataaggggg gttgacatta ttttactgat atgtataata taatttgtat aagaaaatgg   180
agctc                                                              185

<210> SEQ ID NO: 27
<211> LENGTH: 185
<212> TYPE: DNA
<213> ORGANISM: Bacillus

<400> SEQUENCE: 27
ggccttaagg gcctgcaatc gattgtttga gaaaagaaga agaccataaa aataccttgt    60
ctgtcatcag acagggtatt ttttatgctg tccagactgt ccgctgtgta aaaatagga   120 ataaggggg gttgacatta ttttactgat atgtataata taatttgtat aagaaaatgg   180
agctc                                                              185

<210> SEQ ID NO: 28
<211> LENGTH: 33
<212> TYPE: DNA
<213> ORGANISM: Bacillus

<400> SEQUENCE: 28
ggccttaagg gcctgctgtc cagactgtcc gct                                33

<210> SEQ ID NO: 29
<211> LENGTH: 20
<212> TYPE: DNA
<213> ORGANISM: Bacillus

<400> SEQUENCE: 29
ccgtcgctat tgtaaccagt                                              20

```
<210> SEQ ID NO: 30
<211> LENGTH: 20
<212> TYPE: DNA
<213> ORGANISM: Bacillus

<400> SEQUENCE: 30
cgacttcctc ttcctcagag                                              20

<210> SEQ ID NO: 31
<211> LENGTH: 33
<212> TYPE: DNA
<213> ORGANISM: Bacillus

<400> SEQUENCE: 31
ggccttaagg gcctgctgtc cagactgtcc gct                               33

<210> SEQ ID NO: 32
<211> LENGTH: 20
<212> TYPE: DNA
<213> ORGANISM: Bacillus

<400> SEQUENCE: 32
ctatgtggcg cggtattatc                                              20

<210> SEQ ID NO: 33
<211> LENGTH: 20
<212> TYPE: DNA
<213> ORGANISM: Bacillus

<400> SEQUENCE: 33
ttcatccata gttgcctgac                                              20
```